(12) United States Patent
Fernandez de Castro et al.

(10) Patent No.: US 8,685,422 B2
(45) Date of Patent: *Apr. 1, 2014

(54) HIGH ALCOHOL CONTENT FOAMING COMPOSITIONS WITH SILICONE-BASED SURFACTANTS

(75) Inventors: Maria Teresa Fernandez de Castro, Brantford, CA (US); Bruce Michael Koivisto, Willsonville, CA (US); Francisco Munoz, Brantford, CA (US)

(73) Assignee: Deb Worldwide Healthcare Inc., Brantford, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/618,024

(22) Filed: Sep. 14, 2012

(65) Prior Publication Data

US 2013/0012595 A1    Jan. 10, 2013

Related U.S. Application Data

(63) Continuation of application No. 11/520,819, filed on Sep. 14, 2006, now Pat. No. 8,309,111, which is a continuation-in-part of application No. PCT/CA2006/000320, filed on Mar. 7, 2006.

(60) Provisional application No. 60/658,580, filed on Mar. 7, 2005.

(51) Int. Cl.
*A01N 25/00* (2006.01)
*A61K 31/74* (2006.01)
*A61K 51/00* (2006.01)
*A61M 36/14* (2006.01)

(52) U.S. Cl.
USPC .................. 424/405; 424/1.65; 424/78.07

(58) Field of Classification Search
USPC .................... 424/405, 1.65, 78.07
See application file for complete search history.

(56) References Cited

U.S. PATENT DOCUMENTS

| 5,145,977 | A | | 9/1992 | Petroff et al. | |
| 5,439,682 | A | * | 8/1995 | Wivell et al. | 424/401 |
| 5,843,881 | A | * | 12/1998 | Dubois et al. | 512/1 |
| 5,951,993 | A | * | 9/1999 | Scholz et al. | 424/405 |

FOREIGN PATENT DOCUMENTS

| EP | 0 117 889 | 11/1987 |
| WO | 00 57735 | 10/2000 |

OTHER PUBLICATIONS

Office Action dated Feb. 7, 2013 for Korean Patent Application No. 2007-7022867.
Amendment and Response submitted Feb. 17, 2013 for Japanese Patent Application No. 2008-500017.
Examination Report dated Feb. 26, 2013 from the German Patent Office.
Office Action dated Oct. 10, 2012 from the Chinese Intellectual Property Office.
Response dated Feb. 21, 2013 for Canadian Application No. 2,589,502.
Response dated Apr. 23, 2013 for Canadian Application No. 2,589,502.
Supplementary European Search Report dated Apr. 8, 2013.
Deb Reply, dated Feb. 27, 2013, to Appeal in Opposition to EP1811013.
3M Reply dated Mar. 4, 2013, to Appeal in Opposition to EP1811013.
Gojo Evidence in Opposition to Australian Patent No. 2006252070, dated May 27, 2013.
Marly Skin downloaded from http://www.marley-skin.com/pages/deutsch/produkt.html, dated Sep. 26, 2003.
Patterson, Prevention of sodium lauryl sulfate irritant contact dermatitis by Pro-Q aerosol foam skin protectant, Journal of the American Academy of Dermatology, May, 1999, vol. 40, No. 5, Part 1, pp. 783-785.
Letter dated Dec. 21, 2012 enclosing Statement of Grounds of Opposition in the matter of Australian Patent Application No. 2011224144.
Argument and Amendment regarding Korean Application No. 10-2007-7022867, together with claims, dated Jun. 7, 2013.
Decision of Rejection for Chinese Patent Application No. 200680015637.1 dated Jun. 2013.
Canadian Translation Bureau web page www.btb.termiumplus.gc.ca for CAS No. 125997-17-3, dated May 16, 2013.
Dow Corning Corporation Material Safety Data Sheet for SylGard 309 Silicone Surfactant, revised May 6, 2009.

* cited by examiner

*Primary Examiner* — Mina Haghighatian
*Assistant Examiner* — Helen Chui
(74) *Attorney, Agent, or Firm* — Neal, Gerber & Eisenberg LLP

(57) ABSTRACT

This invention relates to a "high lower alcohol content" (>40% v/v of a $C_{1-4}$ alcohol) liquid composition able to be dispensed as a stable foam with the use of non-propellant foam dispensing devices from non-pressurized containers. The liquid compositions comprise a $C_{1-4}$ alcohol, (>40% v/v), a silicone-based surfactant of at least 0.001% by weight for foaming to prepare a foamable composition, 0-10% w/w of additional minor components added to obtain the desired performance (a foamable composition), and the balance being purified water. The compositions may include emulsifier-emollients and mosturizers, secondary surfactants, foam stabilizers, fragrances, antimicrobial agents, other type of medicinal ingredients, and the like ingredients or additives or combinations thereof commonly added to alcohol gels or foams, aerosol compositions or to toiletries, cosmetics, pharmaceuticals and the like.

15 Claims, No Drawings

HIGH ALCOHOL CONTENT FOAMING COMPOSITIONS WITH SILICONE-BASED SURFACTANTS

CROSS REFERENCE TO RELATED U.S. APPLICATIONS

This patent application is a continuation of U.S. application Ser. No. 11/520,819, filed on Sep. 14, 2006, issued as U.S. Pat. No. 8,309,111, which is a continuation-in-part (CIP) of a U.S. National Phase patent application claiming the benefit of PCT/CA2006/000320 filed on Mar. 7, 2006; which further claims the priority benefit from, U.S. Provisional Patent Application Ser. No. 60/658,580 filed on Mar. 7, 2005, in English, entitled HIGH ALCOHOL CONTENT FOAMING COMPOSITIONS WITH SILICONE-BASED SURFACTANTS, and all applications being incorporated herein by reference in their entirety

FIELD OF THE INVENTION

The present invention relates to compositions with high contents of lower alcohol ($C_{1-4}$) that could be dispensed as a foam both under low pressure from unpressurized containers and from pressurized containers achieved with an aerosol packaging system. The compositions to be dispensed as foams contain a silicone-based surfactant for foaming and when mixed with air provide a stable alcohol foam which can be used for personal disinfecting purposes.

BACKGROUND OF THE INVENTION

Ethanol and/or Isopropyl alcohol and/or n-propyl alcohol compositions with at least 60% percent v/v (approximately 52% by weight of alcohol) are well known to be antibacterial, therefore widely accepted for disinfecting purposes. Nonetheless due to the inherent characteristics of alcohol, it is perceived that the higher the content the better the product and a solution with higher than 60% by volume alcohol content is more desirable.

Alcohol disinfectant solutions are generally thickened in order to eliminate the waste and facilitate spreading the composition throughout the desired area. It is also known that other than gelling agents one can use paraffin or waxes to achieve thickening of a solution with high alcohol concentration. Such a composition with lanolin added to reduce the melting point closer to body temperature is described in U.S. Pat. No. 2,054,989. One of the disadvantages of gels and the above-mentioned type of thick alcohol-containing compositions is that if they do not leave a tacky feeling on the hands after one use (although some do), the effect builds up after repetitive use during the day, making it necessary to eventually wash off the thickeners before continuing the usage of an alcohol antiseptic solution. The present invention if formulated for the above-mentioned type of product does not leave such a feel, and does not need to be washed off after repeated use.

Generally speaking a high alcohol content disinfectant solution disinfects but does not clean. In order to make them disinfect and clean, so much soap would need to be added to the solution that the skin would feel soapy and disagreeable resulting in a formulation that would have little commercial appeal. Nonetheless, a non-irritant skin disinfecting formulation with a high content of a lower alcohol for use as a skin-washing agent has been successfully achieved by combining emulsifiers, surfactants and skin emollients as described in U.S. Pat. No. 5,629,006.

Surfactants other than for cleaning purposes are also used for spreading an aqueous composition containing one or more active substances rapidly and evenly over a surface due to their wetting properties. The use of good wetting agents definitely improves the efficient use of active substances in different compositions as described in U.S. Pat. No. 5,928,993.

Although a high alcohol content disinfectant solution has good disinfectant characteristics, it has a sharp smell and is generally perceived to cause drying of the skin, characteristics which can also be diminished to a desirable level in the present invention.

A foam product with greater than 40% v/v alcohol, which is easy and safe to use, is desirable over conventional liquid, gel or ointment type composition products. The concentration of alcohol already poses a hazard in itself, and there are many applications in which the perceived risk may be diminished if it could be dispensed as a foam. A foam intended to be useful as a skin disinfecting agent must have a uniform consistency, spreadability, cleansing ability, and have a pleasant feel, i.e. have rapid breaking power when pressure is applied; all of which present a challenge for a high lower alcohol content composition.

The description of an aqueous foaming skin disinfecting composition using 15% w/w alcohol as a co-solvent, which requires no pressurized container or added propellant to produce the foam, is described in U.S. Pat. No. 3,962,150.

The foam-forming agents utilized heretofore, have been incapable of forming stable foams when the liquid phase has high alcohol content without using other ingredients. Furthermore, lower alcohols have been considered to be defoamers rather than foam-promoting chemicals. According to Klausner, in U.S. Pat. No. 3,131,153, if more than 64% alcohol is used non-homogeneous compositions are obtained. The compositions in the patent required propellant to foam and the foams produced were of limited stability.

Various examples of compositions with a high content of a lower alcohol that are dispensed as a foam have been described, although for the purpose of the present invention the concentrations of alcohol and the levels of other ingredients are not suitable. More importantly, the use of propellants and aerosol containers to generate the foam is not desirable. For example, the compositions described in U.S. Pat. No. 5,906,808 disclose a product that uses an emulsifying wax NF, and a combination of stearyl and cetyl alcohol, or other wax combinations, which improve the foaming performance of the composition, in combination with cetyl lactate, to produce a 0.8% chlorhexidine gluconate alcohol product.

U.S. Pat. No. 5,167,950 issued to Lins discloses a foam product which requires a propellant and where no surfactant is added as a cleaning agent. The composition disclosed in this patent is based upon using an emulsifier system (fatty alcohol ROH 16-22 carbons) in combination with the use of a thickening agent (carbomer, klucel, etc.) to produce an antimicrobial aerosol mousse having a high alcohol content. The mousse includes alcohol, water, a polymeric gelling agent and a surfactant system comprising a C16-C22 alcohol, aerosol propellant and a non-ionic polyethoxylated surfactant.

U.S. Pat. No. 5,629,006 is directed to skin disinfecting compositions using alcohol, block copolymers which include polydimethyl siloxane-polyethylene oxide which contribute to antifoaming, and foaming surfactants such as ammonium lauryl sulfosuccinate. The formulations include thickening agents and the goal is to produce a disinfectant that foams like ordinary soap. The resulting product must be washed or rinsed off the user's skin.

Canadian Patent No. 2,534,692 is directed to a parasiticidal composition for head lice and requires a bio adhesive and is directed to head lice in which the bio adhesive is a high molecular weight carbomer related material which is used because they exhibit pediculicidal and ovicidal activity for killing lice and lice eggs respectively. Similarly to the previous referenced U.S. patent, the alcohol in this composition is only used as a carrier to deliver the carbomer/thickening agent which is the agent responsible for the killing activity sought by the inventors. As for the mixture with silicone, this is not present in all examples and when the silicone material and the alcohol are used the level of thickening agent would made it not possible for the composition to foam and the alcohol level is also below the desired disinfecting level that the present invention teaches.

Despite the work done to date it has been shown that there is little specific knowledge on how foams react and are formed, and surprisingly formulations that might seem not foamable result in the best foam producing ones while other formulations which seemed to have been producing foam even while being prepared did not perform well at all in some non-aerosol foam dispensers. The behaviour of aqueous foams is not the same as that of an alcohol foam.

Silicone-based surfactants have been used in applications requiring lowering of the surface tension and increased wetting properties, especially in applications that require materials to be compatible with solvent systems other than water and non-reactive to other components in the compositions. Silicone surfactants are desirable since they can achieve relatively low surface tension levels with relatively low concentrations in the compositions of interest. Commercial examples of the exploitation of the advantage of the low surface tension levels achieved using silicone based surfactants are crop protection products, printing inks, paints, floor coatings, etc. The characteristics mentioned above make silicone surfactants a candidate for the invention of this patent.

It would be very advantageous to have alcohol based disinfecting formulations containing silicone-based surfactants which may be dispensed as a foam under low pressure conditions and/or through an aerosol packaging system. Further, it would be very advantageous and desirable to find a foaming agent that could be used in concentrations that would allow it to be used in products that can remain in the area on which they have been applied and do not need to be rinsed or wiped off due to small amounts of residue remaining after evaporation. Thus it would also be very advantageous to provide foams that do not leave an unpleasant sticky after-feel as most commercial alcohol gel products are known to, or which clog up the dispensing equipment used to dispense the foams. Silicone-based surfactants are more than desirable for the purpose aforementioned since they are currently used as desirable cosmetic ingredients in creams, lotions, and other cosmetics due to their soft after-feel and properties.

SUMMARY OF THE INVENTION

The present invention provides high alcohol content compositions, which contain a surfactant/cleaning agent as well as a disinfectant/cleaning/solvent/carrier that causes very little drying to the skin or the hands of the user and is able to be dispensed as a foam from both pressurized and non-pressurized dispensing systems.

The present invention provides high alcohol content compositions that are able to be dispensed as a foam which is readily spread over the desired surface for the particular application. The present compositions can be formulated as an antimicrobial alcohol foam. The foamable compositions when dispensed from a suitable dispenser are stable and do not require the use of propellants and pressurized containers although if used would also foam.

Accordingly, the present invention provides a foamable alcohol composition, comprising;
a) a $C_{1-4}$ alcohol, or mixtures thereof, present in an amount greater than about 40% v/v of the total composition;
b) an effective physiologically acceptable silicone-based surface active agent for foaming and wetting selected from the group consisting of Bis-PEG-[6-9] dimethicones, organofunctional siloxanes, linear and/or multifunctional silicone polyethers, silicone sulfosuccinates, silicone alcohol alcoxylates, silicone taurine derivatives, silicone phosphobetaines, silicone quats and combinations thereof, present in an amount of at least 0.01% weight percent of the total composition; and
c) water present in an amount to balance the total composition to 100% weight percent.

In another aspect of the invention there is provided a silicone surfactant composition concentrate, comprising;
a) an effective physiologically acceptable silicone-based surface active agent selected from the group consisting of Bis-PEG-[6-9] dimethicone, organofunctional siloxanes, linear and/or multifunctional silicone polyethers, silicone sulfosuccinates, silicone alcohol alcoxylates, silicone taurine derivatives, silicone phosphobetaines, silicone quats and combinations thereof, present in an amount from 0.01 to about 15.0% by weight percent of the total composition;
b) a foam stabilizing agent present in a range from about 0.01 to about 10.0%;
c) one of moisturizers, emollients and combinations thereof present in a range from about 0.05% to about 5.0%; and
d) water.

The present invention also provides a foamable alcohol composition, comprising;
a) ethanol present in a range from about 20 to about 80% v/v;
b) an effective physiologically acceptable silicone-based surface active agent selected from the group consisting of Bis-PEG-[6-20] dimethicone, 3-(3-Hydroxypropyl)-heptamethyltrisiloxane, ethoxylated, acetate; a Bis-PEG/PPG 18/6 Dimethicone; polyether-modified polysiloxanes; polysiloxane betaines; organofunctional siloxanes and combinations thereof, present in a range from about 0.01% to about 10.0% by weight of the total composition; and
c) a foam stabilizing agent present in a range from about 0.05 to about 1.0% by weight;
d) water present in an amount to balance the total composition to 100% weight percent.

The present invention also provides a method for personal disinfection comprising:
applying to a person's skin a skin-disinfecting alcohol foam composition which comprises
a) air mixed with
b) a liquid comprising
i) a $C_{1-4}$ alcohol, or mixtures thereof, present in an amount greater than about 60% v/v of the total composition;
ii) water present in an amount to balance the total composition to 100% by weight; and
iii) a physiologically acceptable silicone-based surface active agent for foaming and wetting selected from the group consisting of Bis-PEG-[6-9] dimethicones, organofunctional siloxanes, linear and/or multifunctional silicone polyethers, silicone sulfosuccinates, silicone alcohol alcoxylates, silicone taurine derivatives, silicone phosphobetaines, silicone quats and combinations thereof, present in an amount of at least 0.01% weight percent of the total composition.

The present invention also provides a method for producing, and applying to a person's skin, a skin-disinfecting alcohol foam composition, comprising:

a) combining an alcohol $C_{1-4}$, or mixtures thereof, present in an amount greater than about 60% v/v of the total composition with a physiologically acceptable silicone-based surface active agent for foaming and wetting selected from the group consisting of Bis-PEG-[6-9] dimethicones, organofunctional siloxanes, linear and/or multifunctional silicone polyethers, silicone sulfosuccinates, silicone alcohol alcoxylates, silicone taurine derivatives, silicone phosphobetaines, silicone quats and combinations thereof, present in an amount of at least 0.01% weight percent of the total composition, and water present in an amount to balance the total composition to 100% by weight to form an alcohol-silicone surfactant mixture and storing said composition in an unpressurized dispenser having a dispenser pump;

b) activating the dispenser pump to combine the alcohol/silicone-based surfactant mixture with air such that the composition foams as it is dispensed using the dispenser pump under low pressure conditions; and c) applying the foam to the skin.

DETAILED DESCRIPTION OF THE INVENTION

Definitions

The term "emollient" as used herein refers broadly to materials which are capable of maintaining or improving the moisture level, compliance, or appearance of the skin when used repeatedly.

The term "emulsifier" as used herein refers to surfactants or other materials added in small quantities to a mixture of two miscible liquids for the purpose of aiding in the formation and stabilization of an emulsion.

The phrase "emulsifying ingredients" as used herein is synonymous with emulsifier defined above.

The term "emulsion" as used herein refers to a colloidal dispersion of one liquid in another.

The term "surfactant" as used herein is the widely employed contraction for "surface active agents" which is the descriptive generic term for materials that preferentially adsorb at interfaces as a result of the presence of both, lipophilic and lipophobic structural units, the adsorption generally resulting in the alteration of the surface or interfacial properties of the system.

Siloxanes refer to a group of compounds containing silicon atoms bound to oxygen atoms, with organic groups linked to the silicon atoms which are four-coordinate, e.g. $(-R_2Si-O)_n$ where R is an organic group. Silicones are polymers of siloxanes (polysiloxanes). The silicone chain can also be described as any organosilicon oxide polymer in which the structural unit is the siloxane: $(-R_2Si-O)_n-)$. R can be an alkyl (or aryl) group including but not limited to methyl, ethyl and phenyl for example. R may be an alkyl group or a functional group where the alkyl groups may range from C1 to C18 or combinations of these functional groups.

Silicones are unique compounds both in terms of their chemistry and in their wide range of useful applications. Some of their properties include low surface tension, high lubricity, enhanced softness, chemical inertness, low toxicity and non-stick properties. They are also less temperature sensitive than most organic compounds due to the strength and flexibility of the Si—O bond, its partial ionic character and the low interactive forces between the non-polar methyl groups, characteristics that are directly related to the comparatively long Si—O and Si—C bonds. The length of the Si—O and Si—C bonds also allows an unusual freedom of rotation, which enables the molecules to adopt the lowest energy configuration at interfaces, providing a surface tension that is substantially lower than organic-based products. The strength of the silicon-oxygen bond not only gives it its thermal stability, but also a chemical inertia, making it highly resistant to oxidizing and to ultraviolet radiation, ozone and electrical discharges.

The term "silicone-based surfactant" as used herein refers to a silicone surfactant or surface active agent which at very low concentrations, markedly reduce the interfacial surface tension of liquid-gas, liquid-liquid and liquid-solid interfaces. Depending upon their behaviour, at such interfaces surfactants can function as wetting agents, emulsifiers, detergents, dispersants, foaming agents, solubilizers, etc. and therefore useful in many industrial applications. Surfactants have two distinct components in their molecular structure: a hydrophobic (water-repelling) portion and a hydrophilic (water-attracting) portion. The combination of these distinct hydrophobic and hydrophilic parts within a single molecule accounts for the reduced surface tension and other important properties that are characteristic of this group of chemical compounds. Traditional surfactants have carbon chains as the hydrophobic portion of the molecule. The hydrophile that is added to the carbon chain will determine the solubility and the general class of surface active agents as anionic, cationic, non-ionic or amphoteric.

In a silicone surfactant the hydrophobic or lipophilic chain contains a siloxane backbone. Due to the functionality of the molecules tried, the term "silicone-based surfactant" also includes silicone polyethers, also known as dimethicone copolyols in the personal care industry. They contain both a water-insoluble silicone backbone and a number of water-soluble polyether pendant groups. The ratio of the silicone to polyether, and the molecular weight and composition of the components determine the solubility and the specific properties of a product. These products exist as multi-pendant and linear-difunctional polymers. The alkylated silicone may be co-reacted with polyethers to make them either fully or partially soluble in water. Also ethoxy and propoxy-based silicones and alkylated silicones as well as polyether silicone compounds have been shown to work as viable silicone surfactants for the purpose of foaming alcohol.

The phrase "foam stabilizer" as used herein refers to an additive that increases the amount or persistence of foam produced by a surfactant system.

The term "disinfect" as used herein means to destroy or reduce harmful microorganisms.

The phrase "physiologically acceptable" as used herein means a material that does not usually produce irritation or toxicity when applied to the skin and is acceptable by users to apply to human skin and does not usually cause a toxic or irritation reaction when used in the amounts contemplated by the present invention, and is generally recognized by those skilled in the art as a material suitable to use in a cosmetic product.

"Foam" as used herein means a liquid and a gas mixed to form a mass of small bubbles that has a structure that lasts for a variable length of time.

A bubble is a cell of gas surrounded by a film of liquid.

The term "aerosol" as used herein means a package and delivery system, and the product delivered, in which a pressurized gas is used to force the product out for dispensing. The gas may or may not be dispensed with the product.

An "aerosol foam" is a foam dispensed out of an aerosol package and delivery system as defined above.

The phrase "dispensing under low pressure conditions" in the context of producing a foam as used herein means using the pressures that are generated when the liquid formulation is dispensed from an unpressurized container by the user activating a mechanical pump or by squeezing the container to eject the liquid, which in both cases acts to force the liquid out through the container exit as it is mixed with gas, usually air, which produces the foam. These pressures are usually around an atmosphere when being stored and may be increased by the action of activating the dispenser pump which mixes the air with the liquid when discharging the foam. This is distinct from the case where the foams are stored in aerosol containers or other pressurized containers such that when foams are dispensed from the aerosol containers the foam is considered to be being dispensed "under high pressure" conditions. The manually actuated pump could be automated and/or actuated by an external force, such as an electric motor that simply replaces the action of a user manually operating the pump, without changing the overall principle of dispensing the foam from an unpressurized container.

The present invention provides foamable alcohol compositions which include silicone-based surfactants with high contents of lower alcohol ($C_{1-4}$) able to be dispensed as a foam under low pressure conditions from unpressurized containers and through an aerosol packaging system. The present foamable compositions when mixed with air deliver a stable foam to provide an alcoholic liquid solution which can be used for personal disinfecting purposes and which breaks on pressure application such as when a user rubs their hands or when applied over a surface. All percentages provided herein are based on the total weight unless otherwise indicated.

The alcohol used in the present invention is a lower hydrocarbon chain alcohol such as a $C_{1-4}$ alcohol. The preferred alcohol is chosen from ethanol, 2-propanol, or n-propanol, most preferably ethanol, well accepted by Health Care personnel as an adequate disinfectant at the right percentages. It will be appreciated by those skilled in the art that if the alcohol used in the formulation is ethanol or a combination of ethanol with one or more of the other $C_{1-4}$ alcohols the ethanol preferably will be properly denatured to meet the local regulations of the targeted markets, but for the purposes of this patent it will be referred just as ethanol without it being specific as to whether it has been denatured. The compositions may use a single alcohol or as mentioned a blend of two or more alcohols may comprise the alcohol content of the composition.

A significant and very surprising achievement of the present invention is that compositions suitable for disinfecting have been made containing greater than 40% v/v alcohol and a silicone-based surfactant able to be dispensed as a cosmetically appealing foam from both, low pressure conditions and through an aerosol packaging system.

The use of a silicone-based surfactant is the key ingredient as the primary foaming agent in the compositions designed to foam. Silicone surfactants have various interesting properties such as leaving little residue, being able to function in harsh chemical and thermal environments; they have an unparalleled wetting power, characteristics that are in general better than those of traditional surfactants, they show better surface-active properties in organic solvents, and that have made them widely used for applications in coatings, oilfield, material finishes, cleaning, paints, pesticides application, etc.

Traditional surfactants have carbon chains as the hydrophobic portion of the molecule. The hydrophile that is added to the carbon chain will determine the solubility and the general class of surface active agents as anionic, cationic, non-ionic or amphoteric. The silicone-based surfactants suitable for the compositions disclosed herein may include, but are not limited to, phosphate esters, sulphates, polyethers (linear and multifunctional), carboxylates, Imidazoline quats, amino quats, sulfosuccinates, alkyl quats, amino propionates, alcohol alcoxylates, ethoxylates, glycerol esters, amine oxides, acetylenic alcohol derivatives, phosphates, carbohydrate derivatives, sulfonates, betaines, Isethionates, esters, taurine derivatives, phosphobetaines, silicone quats, polyamides, and hydrocarbon surfactants that have a silicone chain.

From the different silicone surfactants commercially available, samples from different manufacturers and different chemical surfactant groups were evaluated. Particularly, the silicone polyethers, also known as dimethicone copolyols showed the best performance. Amongst them, samples of multi-pendant and linear-difunctional showed activity but the later was found to give superior foam properties. This is interesting as well as unexpected since in most water based applications if one of the multi-pendant or linear-difunctional silicone surfactants produces foam in water based mixtures, the other does not perform as well. However this is in agreement with the observations that foaming alcohol compositions behave quite differently from foaming water-based compositions.

While trying different surfactants, mixtures of two or more were evaluated to find out whether there was any synergy identifiable to optimize usage and foam performance. While some synergies were identified, it was also found that particularly difunctional silicone surfactants Bis-PEG [6-20] dimethicones were the best when used alone. The notation Bis-PEG [6-20] means all the Bis-PEG compounds having from 6 to 20 repeating oxyethylene groups. This applies to all other constituents as well. Specifically Bis-PEG 8 dimethicone, Bis-PEG 10 dimethicone, Bis-PEG 12 dimethicone and/or Bis-PEG-20 dimethicone and/or Bis-PEG-17 dimethicone are preferred along with "3-(3-Hydroxypropyl)-heptamethyltrisiloxane, ethoxylated, acetate", also a polyether-modified polysiloxane, a Bis-PEG/PPG 18/6 Dimethicone; and a polysiloxane betaine, showed good results but superior results were obtained with the dimethicone silicone surfactants when the desired concentrations of alcohol are greater than 65% w/w. In general, when using less than 65% w/w of alcohol in the formulations the number of silicone surfactants that produce an acceptable foam is increased and may come from an increased number of different families of silicone surfactants as well.

In preferred embodiments of the compositions, the effective silicone-based surface active agent may be a physiologically acceptable Bis-PEG-[6-20] dimethicone; a 3-(3-Hydroxypropyl)-heptamethyltrisiloxane, ethoxylated, acetate; a Bis-PEG/PPG 18/6 Dimethicone; a Polyether-modified polysiloxane; a Polysiloxane betaine; an organofunctional siloxane; or mixtures thereof from about 0.01% to about 10.0% weight percent of the total composition.

It was surprisingly found that despite the characteristics of silicone-based surfactants, there is little or no information on their use to produce a foamable product with high alcohol content under either low pressure conditions or through an aerosol packaging system.

Furthermore, in order to obtain a high alcohol content product able to produce a foam even if no pressurized containers or propellants are used, surface tension values as low as possible are required so that the pressure required to produce such foam by hand pumps and mechanical means would be sufficient.

During the development of the present invention, it was unexpectedly found that a relatively stable quick breaking foam could be obtained when using just ethanol and the silicone-based surfactant at as high as 80% v/v, while studies using traditional surfactants at a higher percentage yielded results that were quite different and no foam at all could be obtained.

In order to achieve a commercially suitable formulation (one that lasts long enough for the purpose of use in disinfecting applications), reducing the amount of silicone-based surfactant used while using the assistance of other ingredients such as secondary surfactants, emulsifiers, foam stabilizers, fragrances, and the like ingredients employed in cosmetics, aerosols, toiletries, personal care, etc. is one of the approaches that were followed. One of the commercial products obtained uses emulsifiers and polyethoxylated fatty acid surfactants disclosed in U.S. Pat. Nos. 5,167,950 and 6,090, 395, both incorporated herein by reference, while other examples use a combination of different foam stabilizers to achieve a similar result.

Examples of secondary surfactants that may be used in the present compositions include other silicone surfactants, fluorinated surfactants, alkylglucosides, a poly(ethoxylated and/or propoxylated)alcohol, a poly(ethoxylated and/or propoxylated)ester, a derivative of a poly(ethoxylated and/or propoxylated)alcohol, a derivative of a poly(ethoxylated and/or propoxylated)ester, an alkyl alcohol, an alkenyl alcohol, an ester of a polyhydric alcohol, an ether of a polyhydric alcohol, an ester of a polyalkoxylated derivative of a polyhydric alcohol, an ether of a polyalkoxylated derivative of a polyhydric alcohol, a sorbitan fatty acid ester, a polyalkoxylated derivative of a sorbitan fatty acid ester, a betaine, a sulfobetaines, imidazoline derivatives, aminoacid derivatives, lecithins, phosphatides, some amine oxides and sulfoxides and mixtures thereof, present in an amount between about 0.10% to about 5% weight percent.

A preferred betaine is cocamidopropyl betaine. A preferred alkylglucoside is cocoglucoside. A preferred fluorinated surfactant is DEA C[8-18] perfluoroalkylethyl phosphate; another preferred fluorinated surfactant is Ammonium C[6-16] perfluoroalkylethyl phosphate, Preferred polyethoxylated fatty alcohols are polyethoxylated stearyl alcohol (21 moles ethylene oxide) and polyethoxylated stearyl alcohol (2 moles ethylene oxide), and a combination of these two.

The compositions may include an antimicrobial agent. The following antimicrobials are offered as non-limiting examples of suitable antimicrobials for use in the present invention and may include chlorhexidine salt, iodine, a complexed form of iodine, parachlorometaxylenol, triclosan, hexachlorophene, a phenol, behenyl alcohol, a surfactant having a long chain hydrophobic group and a quaternary group, hydrogen peroxide, silver, a silver salt, silver oxide, other quaternary ammonium salts and mixtures thereof.

A preferred antimicrobial agent in the present compositions is chlorhexidine gluconate (CHG) present in an amount between about 0.10% to about 4.0% weight percent. Another preferred antimicrobial agent is didecyl dimethyl diamonium chloride in an amount between about 0.05% to 5% weight percent. Another preferred antimicrobial agent is Benzalkonium chloride in an amount between about 0.05% to 5% weight percent. Another preferred anitimicrobial is Behenyl alcohol between 0.05-15% weight percent.

If the amount of ingredients employed is little enough not to leave a tacky feeling after the composition evaporates after single or multiple uses, and this is achieved while maintaining at least 60% v/v ethanol or n-propanol concentration or 70% v/v isopropanol, then the composition would be ideal for use as an alcohol hand sanitizer/disinfectant foamable composition.

The addition of water to the alcohol produces a more stable foam while allowing to reduce the amount of silicone-based surfactant required to foam the product. For example, using 0.5 to 1.0% silicone-based surfactant with a 50 to 60% v/v alcohol water solution produces a stable foam that does not readily collapse and that produces a stable puff that does not fall even when inverted and does not collapse until pressure is applied (such as when rubbed in hands or on over a surface) to provide an alcoholic liquid solution, while levels of up to 5% are required if the percentage of alcohol used is greater than 65% w/w.

The use of a mild non-irritant surfactant widely used in the cosmetic industry such as cocamidopropyl betaine or a fluorinated surfactant such as DEA C[8-18] perfluoroalkylethyl phosphate or Ammonium C[6-16] perfluoroalkylethyl phosphate as a secondary surfactant is more suitable to prepare the foamable hydroalcoholic composition of the present invention depending on the silicone-based surfactant being used.

In order to stabilize the foam, foam stabilizers, as well as emulsifying ingredients have been tried with good results in allowing the product to be dispensed as a foam even when no propellant and/or pressurized container systems are used.

Examples of compatible foam stabilizers that can optionally be employed include lactic acid esters of monoglycerides, cationic emulsifiers, triquaternized stearic phospholipid complex, hydroxystearamide propyltriamine salts, lactic acid monoglycerides, food emulsifiers such as glyceryl monostearate, Behentrimonium chloride, Cetrimonium chloride, propylene glycol monostearate, glycols, sodium stearoyl lactylate, silicone wax, an encapsulated oil, Microcapsule Mineral Oil.

A preferred foam stabilizer used in the present foamable compositions is cetyl betaine. Another preferred foam stabilizer is glycerine. Another preferred foam stabilizer is Cetrimonium chloride and also Behentrimonium chloride.

Examples of moisturizers and/or emollients which may be used in the present formulations include lanolin, vinyl alcohol, polyvinyl pyrrolidone and polyols selected from the group consisting of glycerol, propylene glycol, glyceryl oleate and sorbitol, cocoglucoside or a fatty alcohol selected from the group consisting of cetyl alcohol, stearyl alcohol, lauryl alcohol, myristyl alcohol and palmityl alcohol, cetyl alcohol, ceteareth 20, and combinations thereof, present in an amount up to about 5%. The compositions may include a lipid layer enhancer such as a mixture of alkylglucoside and glyceryl Oleate, or PEG-200 Hydrogenated Glyceryl Palmiate, or Dihydroxypropyl PEG-5 Linoleammonium Chloride or PEG-7 Glyceryl Cocoate.

The compositions are formulated to be dispensed as a foam from an unpressurized dispenser having a dispenser pump for mixing the composition with air and dispensing foam therefrom. Alternatively the composition may be packaged in an aerosol container and dispensed under high pressure conditions.

The present invention is unique in that it can be dispensed as a foam from such manual low pressure dispensing systems as described, however, the composition can alternatively be dispensed under high pressure systems as well.

The composition may include an aerosol propellant in an amount from about 3 to about 20 weight percent of the total composition for pressurized discharge of the foam. The aerosol propellant may include propane, carbon dioxide, butane, dichloro difluoro methane, dichloro tetra fluoro ethane, octafluorocyclo butane; 1,1,1,2-tetrafluoroethane; 1,1,1,2,3, 3,3 heptafluoropropane, and 1,1,1,3,3,3,-hexafluoropropane. When stored in a metal container with propellant, the formulation may include a corrosion inhibitor such as sorbic acid, benzoic acid, potassium sorbate and sodium benzoate, in an amount from about 0.1 to about 5 weight percent of the total composition.

The inventors have very surprisingly discovered that it is possible to produce alcohol foams which include a combination of both the silicone surfactants disclosed herein and fluorosurfactants disclosed in copending U.S. patent application Ser. No. 10/952,474, filed: Sep. 29, 2004 and PCT Publication WO 2005/030917 A1, the contents of each being incorporated herein by reference, with the resulting foam exhibiting an interesting synergy with respect to the foam quality.

While both types of surfactants in the extremes of the concentrations of alcohol covered produce more and better foam when the alcohol concentration is closer to 40% and produce a lower quality foam that does not last in concentrations higher than 80% it was very interestingly found that the foam quality observed with fluorosurfactants is different from that obtained using silicone based surfactants.

With the pumps used for the examples, compositions using fluorinated surfactants are as described as an aereated "quick" breaking foam disappearing within seconds depending on the amount of alcohol and percentage of surfactant used, while with the silicone based surfactants the foam has a distinctive different appearance, it appears to be more dense and sometimes looks more uniform giving the appearance to be "whiter" not necessarily because there might seem to be more bubbles but because the bubbles last longer, they are more stable.

The difference is better observed when comparing side-by-side samples containing the same percentage of alcohol, and while it is evident that when the foam is first dispensed it shows more volume and a "better" quality appearance if a fluorinated surfactant is used, this visual advantage is observed only during the first few seconds since the foam quite rapidly breaks down to a smaller volume to more resemble the foam obtained with the silicone-based surfactant. The most important difference appears to be how long the foam containing only the silicone-based surfactant lasts compared to the time the foam lasts with a foam containing only the fluorinated surfactant.

It should also be noted that one of the main differences in using one surfactant or the other (fluorosurfactants versus silicone surfactants) is the fact that fluorinated surfactants can reduce the surface tension to lower levels than those achieved using silicone-based surfactants alone, therefore compositions with only silicone based surfactants generally need a higher percentage of the silicone based surfactants to achieve a similar result.

A significant advantage to mixing both types of surfactants in the same composition is that the silicone based surfactant gives a longer lasting effect while the fluorinated surfactant has a better tolerance at higher levels of alcohol hence when mixed the combination provides an improvement in foam quality greater than obtaining using either one individually under some conditions.

Combining the surfactants allows the achievement of the desired foaming effect without exceeding solubility limits of either surfactant while at the same time taking advantage of the particular characteristics of the foam differences produced by each one.

The combination of silicone-based surfactants and fluorinated surfactant is of increasing advantage as the alcohol concentration increases, which is desirable to improve the microbiological efficacy.

The following non-limiting examples are set forth to show for the various preferred embodiments and are not in any way to limit the scope of the present invention.

EXAMPLES

Examples 1 through 12 were prepared to illustrate the ability to produce alcohol-based disinfecting formulations which can be dispensed as foams using different surfactants and a solution of water and 50% ethanol. Examples 13 through 16 illustrate increasing concentrations of a silicone-based surfactant to produce foam with 40% ethanol. Examples 17 through 32 show increasing concentrations of ethanol with different silicone-based surfactants to produce foam. Examples 33 through 36 illustrate increasing concentrations of a silicone-based surfactant to produce acceptable foam at 62% ethanol. Examples 37 through 52 illustrate the ability to produce foam using different surfactants and a solution of 70% v/v Isopropanol. All parts and percentages are expressed by weight unless otherwise indicated.

Comparatively, it was also found that for instance, Cocamidopropyl betaine (CAPB) alone even at 40% ethanol and at 3% CAPB, was unable to produce as good results as those with 60% v/v ethanol, and Silicone-based surfactants using much less percentage (less than 1.0%). Cocamidopropyl betaine does not give any acceptable foam above that percentage of alcohol and the lower than 60% v/v alcohol content makes it inadequate for a sanitizing solution. Also the solution left an unacceptable feeling on the skin after the alcohol evaporated (i.e. a soapy sticky feeling) indicating high levels of surfactant. Advantageously, the afterfeel of the present compositions was not only not soapy but actually pleasant makes the present invention suitable for many different applications.

The following examples were intended to evaluate the foaming ability of different groups of silicone surfactants with different combinations of ethanol, n-propyl alcohol and Isopropyl alcohol. They were also designed to asses the effect in the after feel as well as in the foam quality of some emollients and humectants, lipids, and other cosmetic type desired ingredients to be used with a leave-on hand sanitizer product. Some ingredients with antibacterial properties were also added to again evaluate their effect on foam quality and after feel.

Examples 53 to 293 have total alcohol contents from 61% w/w to 75% w/w. The best foam was achieved with only ethanol as the alcohol, with the next best being the combination Ethanol and n-propyl alcohol using up to 10% n-propyl alcohol. The worst foams were those obtained using only Isopropyl alcohol and/or n-propyl alcohol. Also interesting is the fact that the surfactant that works the best with just ethanol is not the same that works the best with the other 2 alcohols tried. More specifically it was found that the PEG-17-Dimethicone as well as the Bis-PEG/PPG 18/6 Dimethicone work better than the Bis-PEG 12-Dimethicone with just n-propyl alcohol and/or Isopropyl alcohol. While combining different silicone surfactants if different alcohols are used seems to show a synergy to boost the foam when the addition of another alcohol disrupts the foaming ability of a particular silicone surfactant in the end the preferred silicone for the combination of alcohols emollients and other ingredients lies amongst the Bis-PEG [6-20] Dimethicone silicone surfactants.

Combinations of silicone surfactants with other surfactants were also tried; various experiments showed that although it was possible to find acceptable foam quality improvement when using other surfactants, the soapy after-feel was unacceptable for a leave-on product for many surfactants. However the compositions combining silicone surfactants with fluorosufactants mentioned above showed an improvement that very advantageously allows for the reduction in the percentage of silicone surfactant to optimize percentages in the formulation regarding cost and other efficacy desired outcomes.

While some cosmetic ingredients like Cocoglucoside Glyceryl Oleate appear to deteriorate the foam quality when present in the composition, if the after-feel effect is beneficial increasing then the foam quality may be improved by increasing the percentage of surfactant present and/or adding a foam stabilizer to the composition to improve the foam quality and take advantage of the beneficial effect of such cosmetic type ingredient to counteract the undesired after-feel of only using alcohol.

It was also interesting to find that while a higher percentage of silicone surfactant present in the composition has been observed to increase the quality of the foam, the increased amount of silicone surfactant present has to be considerable before an improvement is observed. For example, the foam quality achieved with 1% was not significantly better with 1.5% but was considerably better with 2% and the foam quality using 3% or 4% was very similar while 5% was much better than just 3%.

The quality of the dispensed foam can be dependant upon the characteristics of the pump mechanism used for dispensing the foam from a bottle. For instance the quality of the foam was better with the smaller shot size of 0.75 ml than the bigger shot size of 1.5 ml from an off the shelf foam pump for the same size bottle. The shot size is the amount of liquid dispensed when the pump is activated.

From the above examples it can be concluded that they are clearly denoting how the art of foaming alcohol is different from that of foaming water based composition in more than one aspect and that unexpected outcomes could arise depending on the combination of ingredients desired for the final formulation in combination with the type of foaming device/mechanism to use.

Below are some more specific examples for compositions following a formulation to produce alcohol/silicone-surfactant hand/skin sanitizing foamable compositions; more than one being a foamable disinfecting composition with only alcohol being the only disinfectant ingredient, while other foamable disinfecting compositions use an added antimicrobial such as Chlorhexidine Digluconate or Didecyl Dimethyl Diammonium Chloride, Benzalkonium Chloride, Behenyl alcohol, etc.

Example 294

Alcohol Hand Sanitizing Foamable Disinfecting Composition 0.01-5.0% * silicone-based surfactant (primary surfactant)
0.01-1.0% cocoamidopropylbetaine (secondary surfactant)
0.05-1.0% cetyl betaine (foam stabilizing agent)
0.10-1.5% emulsifier fatty alcohol ROH 16-22 carbons or combination that works well in a final formulation containing
60-70% v/v ethanol
Q.S. water
*Preferably any one of Bis-PEG-[6-20] Dimethicone; a 3-(3-Hydroxypropyl)-heptamethyltrisiloxane, ethoxylated, acetate; a Bis-PEG/PPG 18/6 Dimethicone; a Polyether-modified polysiloxane; a Polysiloxane betaine; an organofunctional siloxane, or mixtures thereof.

Example 295

Alcohol Hand Sanitizing Foamable Disinfecting Composition Concentrate 0.1-5.0% a physiologically acceptable silicone-based surfactant*; (primary surfactant)
0.001-12.0% 1,3Butyleneglycol, 2-Butoxyethanol, or glycerin (foam stabilizing agents)
0.05-5.0% cocoglucoside, glyceryl oleate (moisturizers, emollients and the like)
60-70% v/v ethanol, n-propanol, isopropanol or a combination thereof
Q.S. water
*Preferably any one of Bis-PEG-[6-20] Dimethicone; a 3-(3-Hydroxypropyl)-heptamethyltrisiloxane, ethoxylated, acetate; a Bis-PEG/PPG 18/6 Dimethicone; a Polyether-modified polysiloxane; a Polysiloxane betaine; an organofunctional siloxane, or mixtures thereof.

Example 296

Alcohol Hand Sanitizing Foamable Disinfecting Composition 0.01-5.0% * silicone-based surfactant (primary surfactant)
0.01-1.0% fluorinated surfactant and or other silicone-based surfactants or mixtures (secondary surfactant/s)
0.05-1.0% Cetrimonium Chloride (foam stabilizing agent)
0.05-1.0% Behentrimonium Chloride (foam stabilizing agent)
0.10-1.5% Dihydroxypropyl PEG-5 Linoleammonium Chloride, Glyceryl Oleate, PEG-200 Hydrogenated Glyceryl Palmate, Behenyl PG-Trimomium chloride, PEG-7 Glyceryl Cocoate or combination of emollients, lipids, humectants that works well in a final formulation containing
1-10% n-propyl alcohol
60-70% v/v ethanol
Q.S. water
*Preferably any one of Bis-PEG-[6-20] Dimethicone; a 3-(3-Hydroxypropyl)-heptamethyltrisiloxane, ethoxylated, acetate; a Bis-PEG/PPG 18/6 Dimethicone; a Polyether-modified polysiloxane; a Polysiloxane betaine; an organofunctional siloxane, or mixtures thereof.

Example 297

Alcohol Hand Sanitizing Foamable Disinfecting Composition 0.01-5.0% * silicone-based surfactant (primary surfactant)
0.05-1.0% Cetrimonium Chloride (foam stabilizing agent)
0.05-1.0% Behentrimonium Chloride (foam stabilizing agent)
0.10-1.5% Dihydroxypropyl PEG-5 Linoleammonium Chloride, Glyceryl Oleate, PEG-200 Hydrogenated Glyceryl Palmate, Behenyl PG-Trimomium chloride, PEG-7 Glyceryl Cocoate or combination of emollients, lipids, humectants that works well in a final formulation containing
1-10% n-propyl alcohol
60-70% v/v ethanol
Q.S. water

*Preferably any one of Bis-PEG-[6-20] Dimethicone; a 3-(3-Hydroxypropyl)-heptamethyltrisiloxane, ethoxylated, acetate; a Bis-PEG/PPG 18/6 Dimethicone; a Polyether-modified polysiloxane; a Polysiloxane betaine; an organofunctional siloxane, or mixtures thereof.

Example 298

Alcohol Hand Sanitizing Foamable Disinfecting Composition 0.01-5.0% * silicone-based surfactant (primary surfactant)
0.01-1.0% fluorinated surfactant and or other silicone-based surfactants or mixtures (secondary surfactant/s)
0.05-1.0% Cetrimonium Chloride (foam stabilizing agent)
0.05-1.0% Behentrimonium Chloride (foam stabilizing agent)
0.10-1.5% Dihydroxypropyl PEG-5 Linoleammonium Chloride, Glyceryl Oleate, PEG-200 Hydrogenated Glyceryl Palmate, Behenyl PG-Trimomium chloride, PEG-7 Glyceryl Cocoate or combination of emollients, lipids, humectants that works well in a final formulation containing
60-70% v/v ethanol
Q.S. water
 *Preferably any one of Bis-PEG-[6-20] Dimethicone; a 3-(3-Hydroxypropyl)-heptamethyltrisiloxane, ethoxylated, acetate; a Bis-PEG/PPG 18/6 Dimethicone; a Polyether-modified polysiloxane; a Polysiloxane betaine; an organofunctional siloxane, or mixtures thereof.

Example 299

Alcohol Hand Sanitizing Foamable Disinfecting Composition 0.01-5.0% * silicone-based surfactant (primary surfactant)
0.05-1.0% Cetrimonium Chloride (foam stabilizing agent)
0.05-1.0% Behentrimonium Chloride (foam stabilizing agent)
0.10-1.5% Dihydroxypropyl PEG-5 Linoleammonium Chloride, Glyceryl Oleate, PEG-200 Hydrogenated Glyceryl Palmate, Behenyl PG-Trimomium chloride, PEG-7 Glyceryl Cocoate or combination of emollients, lipids, humectants that works well in a final formulation containing
60-70% v/v ethanol
Q.S. water
 *Preferably any one of Bis-PEG-[6-20] Dimethicone; a 3-(3-Hydroxypropyl)-heptamethyltrisiloxane, ethoxylated, acetate; a Bis-PEG/PPG 18/6 Dimethicone; a Polyether-modified polysiloxane; a Polysiloxane betaine; an organofunctional siloxane, or mixtures thereof.

Example 300

Chlorhexidine Gluconate (CHG) & Alcohol Hand Sanitizing Foamable Disinfecting Composition Formulation 294, 295, 296, 297, 298 or 299 added with 0.50-4.0% Chlorhexidine Gluconate (CHG)

Example 301

Didecyl Dimethyl Diammonium Chloride & Alcohol Hand Sanitizing Foamable Disinfecting Composition Formulation 294, 295, 296, 297, 298 or 299 added with 0.01-5.0% Didecyl Dimethyl Diammonium Chloride

Example 302

Benzalkonium Chloride & Alcohol Hand Sanitizing Foamable Disinfecting Composition Formulation 294, 295, 296, 297, 298 or 299 added with 0.01-5.0% Benzalkonium Chloride

Example 303

Behenyl Alcohol & Alcohol Hand Sanitizing Foamable Disinfecting Composition

Formulation 294, 295, 296, 297, 298 or 299 added with 0.01-5.0% Behenyl Alcohol

Example 304

Alcohol Hand Sanitizing Foamable Disinfecting Composition 0.01-5.0% * silicone-based surfactant (primary surfactant) a preferred composition is 3%
0.05-1.0% Behentrimonium Chloride (foam stabilizing agent) a preferred composition is 0.1% of 85% conc. therefore is actually 0.085%
0.05-1.5% Dihydroxypropyl PEG-5 Linoleammonium Chloride, a preferred conc. Is 0.05% %
0.05-1.5% PEG-200 Hydrogenated Glyceryl Palmate and PEG-7 Glyceryl Cocoate, a preferred conc. Is 0.08% %
0.05-1.5% Cocoglucoside and Glyceryl Oleate, a preferred conc. is 0.08%
1-60% n-propyl alcohol, a preferred conc. is 10%
20-80% v/v ethanol, a preferred conc. is 65% (where the sum total of both n-popyl alcohol and ethanol is at minimum about 60% and at maximum about 85%, a preferred total conc. is 65%,
Q.S. water
 Preferably any one of Bis-PEG-[6-20] Dimethicone; a 3-(3-Hydroxypropyl)-heptamethyltrisiloxane, ethoxylated, acetate; a Bis-PEG/PPG 18/6 Dimethicone; a Polyether-modified polysiloxane; a Polysiloxane betaine; an organofunctional siloxane, or mixtures thereof.

Example 305

Alcohol Hand Sanitizing Foamable Disinfecting Composition 0.01-5.0% * silicone-based surfactant (primary surfactant) a preferred composition is 2%
0.05-1.0% Behentrimonium Chloride (foam stabilizing agent), a preferred composition is 0.1% of 85% conc. therefore is actually 0.085%,
0.05-1.5% Dihydroxypropyl PEG-5 Linoleammonium Chloride, a preferred conc. Is 0.05% %,
0.05-1.5% PEG-200 Hydrogenated Glyceryl Palmate and PEG-7 Glyceryl Cocoate, a preferred conc. Is 0.08% %, 0.05-1.5% Cocoglucoside and Glyceryl Oleate, a preferred conc. Is 0.08%,
60-80% v/v ethanol, a preferred conc. is 62%
Q.S. water
Preferably any one of Bis-PEG-[6-20] Dimethicone; a 3-(3-Hydroxypropyl)-heptamethyltrisiloxane, ethoxylated, acetate; a Bis-PEG/PPG 18/6 Dimethicone; a Polyether-modified polysiloxane; a Polysiloxane betaine; an organofunctional siloxane, or mixtures thereof.

The process to prepare the compositions of the present invention described herein is straightforward since most of the ingredients are liquid. When wax type ingredients are to be used, they can be incorporated more easily by warming up to their melting temperature, from 40° C. to 70° C. depending on the ingredients preferably to the water portion while mixing and then adding to the alcohol either still warm or after allowing it to cool down or they could be added in "cold", at room temperature to the alcohol before any other ingredient and mixed until completely incorporated before adding the rest of the ingredients according to the composition. Depending on the silicone surfactant used, it could be preferable to add the silicone surfactant to the alcohol prior to adding the other ingredients with the water.

Active ingredients may be pre-dissolved into either the water or the alcohol first, a process that will be well known to anyone skilled in the art. If a specific formulation cannot be adjusted to give the desired quality of foam with the preferred percentages of the different constituents, the characteristics of the dispensing mechanism may be modified to improve foam quality, for example the type and characteristics of the foaming pump, such as changing the air/liquid ratio, screen sizes at the nozzle, to mention a few, can be adjusted in ways which will be apparent to those skilled in the art.

The compositions described herein provide improved alcohol based disinfecting products over commercially available compositions with high concentrations of alcohol, as well as the fact they are able to foam without the use of propellants or pressurized containers, although it will be appreciated that using propellants may in some cases improve the quality of the resulting foam.

Depending on the alcohol concentration and the application of the particular composition the foam produced can widely vary, being at the high end of a relatively fast breaking foam variety which is stable enough to be thoroughly spread onto the skin without undue waste or effort.

The present formulations may be first made as a concentrate with only some of the constituents which can be shipped and then constituted with the remaining constituents. For example, the concentrate can include the effective silicone-based surface active agent for wetting and foaming present in an amount of at least 0.01% weight percent of the total composition 0.01 to about 15.0%, a foam stabilizing agent including at least from about 0.01 to about 10.0%, and any one of moisturizers, emollients and combinations thereof present in a range from about 0.05% to about 5.0%; and water.

The composition concentrate can then be constituted as an alcohol disinfecting composition by adding an alcohol $C_{1-4}$, or mixtures thereof, present in an amount between about 60% v/v to about 80% v/v of the total composition; and b) water present in an amount to balance the total composition to 100% weight percent.

Due to the nature of the base composition with respect to the alcohol concentration and the quality of the ingredients, an advantageous application for the present invention is as an alcohol skin/hand disinfectant composition for a foamable product, examples of which are described above. Nevertheless, the present invention lends itself to the preparation of a wide variety of products for disinfecting applications, and it is to be understood that other embodiments may be utilized and that changes may be made without departing from the scope of the invention.

Consequently, it is intended that the claims be interpreted to cover such modifications and equivalents. To note a few, the following products may be produced using the alcohol/silicone-surfactants: medicated foams, sunscreen foams, hand cream foams, brush-less shaving cream foams, shower or bath oil foams, dry hair shampoo foams, make-up remover foams, analgesic foam rubs, hair grooming foams and antiperspirants hair cleaning foam, antiperspirant foam, hair conditioner foams.

As used herein, the terms "comprises", "comprising", "includes" and "including" are to be construed as being inclusive and open ended, and not exclusive. Specifically, when used in this specification including claims, the terms "comprises", "comprising", "includes" and "including" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

REFERENCES CITED
U.S. PATENT DOCUMENTS

| | | | |
|---|---|---|---|
| 2,054,989 | September 1936 | Moore | 167/58 |
| 3,131,153 | April 1964 | Klausner | 252/305 |
| 3,962,150 | June 1976 | Leonard et al. | 252/542 |
| 4,440,653 | April 1984 | James et al. | 252/8.55 |
| 5,167,950 | December 1992 | Lins | 424/47 |
| 4,956,170 | September 1990 | Lee | 514/772.1 |
| 5,629,006 | May 1997 | Minh et al. | 424/405 |
| 5,906,808 | May 1999 | Osborne, et al. | 424/43 |
| 5,928,993 | July 1999 | Ingegärd | 504/116 |
| 5,951,993 | September 1999 | Scholz et al. | 424/405 |
| 6,090,395 | July 2000 | Asmus et al. | 424/401 |
| 6,610,315 | August 2003 | Scholz et al. | 424/415 |
| 6,623,744 | September 2003 | Asmus et al. | 424/401 |
| 6,562,360 | May 2003 | Scholz et al. | 424/405 |

OTHER PUBLICATIONS

Myers, Drew; "Surfactant Science and Technology", second edition, Drew Myers, VCH Publishers, New York, 1992

Examples 1-6

| Amount Ingredients | Ex. 1 | Ex. 2 | Ex. 3 | Ex. 4 | Ex. 5 | Ex. 6 |
|---|---|---|---|---|---|---|
| Ethanol | 50.00 | 50.00 | 50.00 | 50.00 | 50.00 | 50.00 |
| Silicone-based surfactant | 0.50 | — | — | — | — | — |
| Cocamidopropyl betaine (1) | — | 8.00 | — | — | — | — |
| Alkyl-glucoside (2) | — | — | 8.00 | — | — | — |

-continued

| Amount Ingredients | Ex. 1 | Ex. 2 | Ex. 3 | Ex. 4 | Ex. 5 | Ex. 6 |
|---|---|---|---|---|---|---|
| Alkylglucoside (3) | — | — | — | 8.00 | — | — |
| Glycomul L | — | — | — | — | 8.00 | — |
| Sorbitan Sesquioleate | — | — | — | — | — | 8.00 |
| Purified Water | 49.50 | 42.00 | 42.00 | 42.00 | 42.00 | 42.00 |
| Total % | 100.00 | 100.00 | 100.00 | 100.00 | 100.00 | 100.00 |

(1) Amphoteric,
(2) Nonionic,
(3) Anionic

Examples 7-12

| Amount Ingredients | Ex. 7 | Ex. 8 | Ex. 9 | Ex. 10 | Ex. 11 | Ex. 12 |
|---|---|---|---|---|---|---|
| Ethanol | 50.00 | 50.00 | 50.00 | 50.00 | 50.00 | 50.00 |
| Polysorbate 20 | 8.00 | — | — | — | — | — |
| Polyoxyethylene Sorbitan Monooleate | — | 8.00 | — | — | — | — |
| Sorbitan Monooleate | — | — | 8.00 | — | — | — |
| Cocamidopropyl betaine & sodium caproyl lactate | — | — | — | 8.00 | — | — |
| Cocamidopropyl hydroxysultaine | — | — | — | — | 8.00 | — |
| Sodium Cocoamphoacetate | — | — | — | — | — | 8.00 |
| Purified Water | 42.00 | 42.00 | 42.00 | 42.00 | 42.00 | 42.00 |
| Total % | 100.00 | 100.00 | 100.00 | 100.00 | 100.00 | 100.00 |

Examples 13-16

| Ingredients | Ex. 13 | Ex. 14 | Ex. 15 | Ex. 16 |
|---|---|---|---|---|
| Ethanol | 40.00 | 40.00 | 40.00 | 40.00 |
| Bis-PEG-20 dimethicone | 0.01 | — | — | — |
| 3-(3-Hydroxypropyl)-heptamethyltrisiloxane, ethoxylated, acetate | — | 0.01 | — | — |
| Polyether-modified polysiloxane | — | — | 0.01 | — |
| Polysiloxane betaine | — | — | — | 0.01 |
| Purified Water | 59.99 | 59.99 | 59.99 | 59.99 |
| Total % | 100.00 | 100.00 | 100.00 | 100.00 |

Examples 17-20

| Ingredients | Ex. 17 | Ex. 18 | Ex. 19 | Ex. 20 |
|---|---|---|---|---|
| Ethanol | 40.00 | 50.00 | 60.00 | 75.00 |
| Bis-PEG-20 dimethicone | 0.01 | 0.01 | 0.01 | 8.00 |
| Purified Water | 59.99 | 49.99 | 39.99 | 17.00 |
| Total % | 100.00 | 100.00 | 100.00 | 100.00 |

Examples 21-24

| Ingredients | Ex. 21 | Ex. 22 | Ex. 23 | Ex. 24 |
|---|---|---|---|---|
| Ethanol | 40.00 | 50.00 | 60.00 | 75.00 |
| Polysiloxane betaine | 1.0 | 1.0 | 1.0 | 8.00 |
| Purified Water | 59.00 | 49.00 | 49.00 | 17.00 |
| Total % | 100.00 | 100.00 | 100.00 | 100.00 |

Examples 25-28

| Ingredients | Ex. 25 | Ex. 26 | Ex. 27 | Ex. 28 |
|---|---|---|---|---|
| Ethanol | 40.00 | 50.00 | 60.00 | 75.00 |
| Polyether-modified polysiloxane | 1.0 | 1.0 | 1.0 | 1.0 |
| Purified Water | 59.00 | 49.00 | 39.00 | 24.00 |
| Total % | 100.00 | 100.00 | 100.00 | 100.00 |

Examples 29-32

| Ingredients | Ex. 29 | Ex. 30 | Ex. 31 | Ex. 32 |
|---|---|---|---|---|
| Ethanol | 40.00 | 50.00 | 60.00 | 75.00 |
| 3-(3-Hydroxypropyl)-heptamethyltrisiloxane, ethoxylated, acetate | 0.5 | 0.5 | 0.5 | 10.00 |
| Purified Water | 59.5 | 49.50 | 39.50 | 15.00 |
| Total % | 100.00 | 100.00 | 100.00 | 100.00 |

Examples 33-36

| Ingredients | Amount | | | |
|---|---|---|---|---|
| | Ex. 33 | Ex. 34 | Ex. 35 | Ex. 36 |
| Ethanol | 62.00 | 62.00 | 62.00 | 62.00 |
| Bis-PEG-20 dimethicone | 0.50 | 1.00 | 2.0 | 5.00 |
| Purified Water | 37.50 | 37.00 | 36.00 | 33.00 |
| Total % | 100.00 | 100.00 | 100.00 | 100.00 |

Examples 37-42

| Ingredients | Amount | | | | | |
|---|---|---|---|---|---|---|
| | Ex. 37 | Ex. 38 | Ex. 39 | Ex. 40 | Ex. 41 | Ex. 42 |
| 70% v/v Isopropanol | 99.90 | 92.00 | 92.00 | 92.00 | 92.00 | 92.00 |
| Silicone-based surfactant | 0.10 | — | — | — | — | — |
| Cocamidopropyl betaine (1) | — | 8.00 | — | — | — | — |
| Alkylglucoside (2) | — | — | 8.00 | — | — | — |
| Alkylglucoside (3) | — | — | — | 8.00 | — | — |
| Glycomul L | — | — | — | — | 8.00 | — |
| Sorbitan Sesquioleate | — | — | — | — | — | 8.00 |
| Total % | 100.00 | 100.00 | 100.00 | 100.00 | 100.00 | 100.00 |

(1) Amphoteric,
(2) Nonionic,
(3) Anionic

Examples 43-48

| Ingredients | Amount | | | | | |
|---|---|---|---|---|---|---|
| | Ex. 43 | Ex. 44 | Ex. 45 | Ex. 46 | Ex. 47 | Ex. 48 |
| 70% v/v Isopropanol | 92.00 | 92.00 | 92.00 | 92.00 | 92.00 | 92.00 |
| Polysorbate 20 | 8.00 | — | — | — | — | — |
| Polyoxyethylene Sorbitan Monooleate | — | 8.00 | — | — | — | — |
| Sorbitan Monooleate | — | — | 8.00 | — | — | — |
| Cocamidopropylbetaine & sodium caproyl lactate | — | — | — | 8.00 | — | — |
| Cocamidopropyl hydroxysultaine | — | — | — | — | 8.00 | — |
| Sodium Cocoamphoacetate | — | — | — | — | — | 8.00 |
| Total % | 100.00 | 100.00 | 100.00 | 100.00 | 100.00 | 100.00 |

Examples 49-52

| Ingredients | Amount | | | |
|---|---|---|---|---|
| | Ex. 49 | Ex. 50 | Ex. 51 | Ex. 52 |
| 70% v/v Isopropanol | 99.00 | 99.00 | 99.00 | 99.00 |
| Bis-PEG-20 dimethicone | 1.0 | — | — | — |
| 3-(3-Hydroxypropyl)-heptamethyltrisiloxane, ethoxylated, acetate | — | 1.0 | — | — |
| Polyether-modified polysiloxane | — | — | 1.0 | — |
| Polysiloxane betaine | — | — | — | 1.0 |
| Total % | 100.00 | 100.00 | 100.00 | 100.00 |

The solutions prepared, were evaluated as to whether foam was produced or not and if so, then the foam produced was described as follows:

| Example | Foam Produced | Foam Evaluation/Description/Characteristics |
|---|---|---|
| Ex. 1 | Yes | Very good stable stiff puff creamy and soft lasts a long time |
| Ex. 2 | No | Just Very Wet Bubbles produced lasting <10 seconds |
| Ex. 3 | No | — |
| Ex. 4 | No | — |
| Ex. 5 | No | — |
| Ex. 6 | No | Just Very Wet Bubbles produced lasting <7 seconds |
| Ex. 7 | No | Just Very Wet Bubbles produced lasting <10 seconds |
| Ex. 8 | No | — |
| Ex. 9 | No | Just Very Wet Bubbles produced lasting <10 seconds |
| Ex. 10 | No | — |
| Ex. 11 | No | — |
| Ex. 12 | No | — |
| Ex. 13 | Yes | Quick fast breaking foam lasts more than a minute |
| Ex. 14 | Yes | Very good puff creamy and soft lasts minutes |
| Ex. 15 | Yes | Very good puff creamy and soft lasts minutes |
| Ex. 16 | Yes | Quick fast breaking foam lasts more than a minute |
| Ex. 17 | Yes | Very good puff creamy and soft lasts minutes |
| Ex. 18 | Yes | Good puff creamy and soft lasts minutes |
| Ex. 19 | Yes | Quick fast breaking foam lasts more than a 10 secs |
| Ex. 20 | Yes | — |
| Ex. 21 | Yes | Runny watery foam which lasts more than 45 secs |
| Ex. 22 | Yes | Quick fast breaking foam lasts more than a 10 secs |
| Ex. 23 | Yes | Runny watery foam which lasts more than 20 secs |
| Ex. 24 | Yes | — |
| Ex. 25 | Yes | Runny watery foam which lasts more than 20 secs |
| Ex. 26 | Yes | Runny foam which lasts more than 20 secs |
| Ex. 27 | Yes | Quick fast breaking foam lasts more than a 45 secs |
| Ex. 28 | No | Quick fast breaking foam lasts more than a 45 secs |
| Ex. 29 | Yes | Very good creamy and soft lasts more than a minute |
| Ex. 30 | Yes | Good creamy and soft lasts more than a minute |
| Ex. 31 | Yes | Quick fast breaking foam lasts more than a 45 secs |
| Ex. 32 | No | — |
| Ex. 33 | No | Quick fast breaking foam lasts more than a minute |
| Ex. 34 | No | Good creamy and soft lasts more than a minute |

| Example | Foam Produced | Foam Evaluation/Description/Characteristics |
|---|---|---|
| Ex. 35 | No | Very good creamy and soft lasts more than a minute |
| Ex. 36 | No | Very good creamy and soft lasts minutes |
| Ex. 37 | Yes | Quick fast breaking foam lasts more than a 20 secs |
| Ex. 38 | No | — |
| Ex. 39 | No | — |
| Ex. 40 | No | — |
| Ex. 41 | No | — |
| Ex. 42 | No | — |
| Ex. 43 | No | — |
| Ex. 44 | No | — |
| Ex. 45 | No | — |
| Ex. 46 | No | — |
| Ex. 47 | No | — |
| Ex. 48 | No | — |
| Ex. 49 | Yes | Runny watery foam which lasts more than a 45 secs |
| Ex. 50 | Yes | Runny watery foam which lasts more than a 45 secs |
| Ex. 51 | Yes | Runny watery foam which lasts more than a 45 secs |
| Ex. 52 | Yes | Runny watery foam which lasts more than a 45 secs |

Examples 53-63

| INGREDIENTS | 53 | 54 | 55 | 56 | 57 | 58 | 59 | 60 | 61 | 62 | 63 |
|---|---|---|---|---|---|---|---|---|---|---|---|
| 1,3-butylene glycol | 0.43 | 0.43 | 1 | 1 | 1 | 0.43 | 0.43 | 1 | 1 | 1 | 0.43 |
| Ethanol | 62 | 52 | 52.2 | 62.2 | 42.2 | 62 | 52 | 52.2 | | 42.2 | 62 |
| Benzalkonium Chloride | | | | | | 0.1 | 0.1 | 0.1 | 0.1 | 0.1 | |
| Dimethyl Ammonium Chloride | | | | | | | | | | | 0.1 |
| PEG 17-Dimethicone | 1 | 1 | 1 | 1 | 1 | 1 | 1 | 1 | 1 | 1 | 1 |
| Glycerine | 0.9 | 0.9 | 0.5 | 0.5 | 0.5 | 0.9 | 0.9 | 0.5 | 0.5 | 0.5 | 0.9 |
| Cocoglucoside & Glyceryl Oleate | 0.08 | 0.08 | | | | 0.08 | 0.08 | | | | 0.08 |
| DEA C8-C18 Perfluoroalkylethyl Phosphate | | | | | | | | | | | |
| Ammonium C6-C16 Perfluoroalkylethyl Phosphate | 0.5 | 0.5 | 0.3 | 0.3 | 0.3 | 0.3 | 0.3 | 0.3 | 0.3 | 0.3 | 0.5 |
| Cetrimonium Chloride | | | | | | | | | | | |
| n-Propyl alcohol | 2 | 10 | 10 | | 20 | 2 | 10 | 10 | 62.2 | 20 | 2 |
| Propylene glycol | | | 0.5 | 0.5 | 0.5 | | | 0.5 | 0.5 | 0.5 | |
| Purified Water | 33.1 | 36.1 | 34.6 | 34.6 | 34.6 | 33.2 | 35.2 | 34.5 | 34.5 | 34.5 | 33 |

Examples 64-73

| INGREDIENTS | 64 | 65 | 66 | 67 | 68 | 69 | 70 | 71 | 72 | 73 | 64 |
|---|---|---|---|---|---|---|---|---|---|---|---|
| 1,3-butylene glycol | 0.43 | 0.43 | 1 | 1 | 1 | 0.43 | 0.43 | 0.43 | 0.43 | 0.43 | 0.43 |
| Ethanol | 62 | 62 | 52.2 | 52.2 | 52.2 | 62 | 52 | 62 | 62 | 62 | 62 |
| Benzalkonium Chloride | | | | | | | | | | | |
| Dimethyl Ammonium Chloride | 0.5 | 1 | 0.1 | 0.1 | 1 | | | | | | 0.5 |
| PEG 17-Dimethicone | 1 | 1 | 1 | 1 | 1 | 1 | 1.5 | 1 | 1 | 1 | 1 |
| Glycerine | 0.9 | 0.9 | 0.5 | 0.5 | 0.5 | 0.9 | 0.9 | 0.9 | 0.9 | 0.9 | 0.9 |
| Cocoglucoside & Glyceryl Oleate | 0.08 | 0.08 | | | | 0.08 | | 0.08 | 0.08 | 0.08 | 0.08 |
| DEA C8-C18 Perfluoroalkylethyl Phosphate | | | | | | | 0.3 | 0.5 | 0.5 | 0.5 | |
| Ammonium C6-C16 Perfluoroalkylethyl Phosphate | 0.5 | 0.5 | 0.3 | 0.3 | 0.3 | 0.5 | 0.3 | | | | 0.5 |
| Cetrimonium Chloride | | | | | | | | 0.05 | 0.1 | 0.05 | |
| n-Propyl alcohol | 2 | 2 | 10 | 10 | 10 | 2 | 10 | 2 | 2 | 2 | 2 |
| Propylene glycol | | | 0.5 | 0.5 | 0.5 | | | | | | |
| Purified Water | 32.6 | 32.1 | 34.5 | 34.5 | 33.6 | 33.1 | 35 | 33 | 33 | 33 | 32.6 |

Example 74-84

| INGREDIENTS | 74 | 75 | 76 | 77 | 78 | 79 | 80 | 81 | 82 | 83 | 84 |
|---|---|---|---|---|---|---|---|---|---|---|---|
| 1,3-butylene glycol | 0.43 | 0.43 | 0.43 | 0.43 | 0.43 | 0.43 | 0.43 | 0.43 | 0.43 | 0.43 | 0.43 |
| Ethanol | 52 | 62 | 62 | 52 | 52 | 62 | 62 | 52 | 52 | 62 | 62 |
| Glycerine | 0.9 | 0.9 | 0.9 | 0.9 | 0.9 | 0.9 | 0.9 | 0.9 | 0.9 | 0.9 | 0.9 |
| Cocoglucoside & Glyceryl Oleate | 0.08 | 0.08 | 0.08 | 0.08 | 0.08 | 0.08 | 0.08 | 0.08 | 0.08 | 0.08 | 0.08 |
| Bis-PEG 17 Dimethicone | | 5.5 | 5.5 | | | 5.5 | 5.5 | | | 5.5 | 5.5 |
| Bis-PEG 12 Dimethicone | 4.8 | | | 4.8 | 4.8 | | | 4.8 | 4.8 | | |
| Cetrimonium Chloride | 0.1 | | | | | | | | | | |
| Dihydroxypropyl PEG-5 Linoleammonium Chloride | | 0.05 | 0.1 | 0.05 | 0.1 | 0.1 | | | | | |
| Behenoyl PG-Trimonium Chloride | | | | | | 0.05 | 0.1 | 0.05 | 0.1 | | |
| Behenamidopropyl Dimethylamine | | | | | | | | | | 0.05 | 0.1 |
| Behentrimonium Chloride | | | | | | | | | | | |
| Cetearyl Alcohol and Behentrimonium Chloride | | | | | | | | | | | |
| n-Propyl alcohol | 10 | 2 | 2 | 10 | 10 | 2 | 2 | 10 | 10 | 2 | 2 |
| Propylene glycol | | | | | | | | | | | |
| Purified Water | 31.7 | 29 | 29 | 31.7 | 31.7 | 28.9 | 29 | 31.7 | 31.7 | 29 | 29 |

Example 85-94

| INGREDIENTS | 85 | 86 | 87 | 88 | 89 | 90 | 91 | 92 | 93 | 94 |
|---|---|---|---|---|---|---|---|---|---|---|
| 1,3-butylene glycol | 0.43 | 0.43 | 0.43 | 0.43 | 0.43 | 0.43 | 0.43 | 0.43 | 0.43 | 0.43 |
| Ethanol | 52 | 52 | 62 | 62 | 52 | 52 | 62 | 62 | 52 | 52 |
| Glycerine | 0.9 | 0.9 | 0.9 | 0.9 | 0.9 | 0.9 | 0.9 | 0.9 | 0.9 | 0.9 |
| Cocoglucoside & Glyceryl Oleate | 0.08 | 0.08 | 0.08 | 0.08 | 0.08 | 0.08 | 0.08 | 0.08 | 0.08 | 0.08 |
| Bis-PEG 17 Dimethicone | | | 5.5 | 5.5 | | | 5.5 | 5.5 | | |
| Bis-PEG 12 Dimethicone | 4.8 | 4.8 | | | 4.8 | 4.8 | | | 4.8 | 4.8 |
| Cetrimonium Chloride | | | | | | | | | | |
| Dihydroxypropyl PEG-5 Linoleammonium Chloride | | | | | | | | | | |
| Behenoyl PG-Trimonium Chloride | | | | | | | | | | |
| Behenamidopropyl Dimethylamine | 0.05 | 0.1 | | | | | | | | |
| Behentrimonium Chloride | | | 0.5 | 0.1 | 0.05 | 0.1 | | | | |
| Cetearyl Alcohol and Behentrimonium Chloride | | | | | | | 0.05 | 0.1 | 0.05 | 0.1 |
| n-Propyl alcohol | 10 | 10 | 2 | 2 | 10 | 10 | 2 | 2 | 10 | 10 |
| Propylene glycol | | | | | | | | | | |
| Purified Water | 31.7 | 31.7 | 28.6 | 29 | 31.7 | 31.7 | 29 | 29 | 31.7 | 31.7 |

Examples 95-115

| INGREDIENTS | 95 | 96 | 97 | 98 | 99 | 100 | 101 | 102 | 103 | 104 | 105 |
|---|---|---|---|---|---|---|---|---|---|---|---|
| Dimethicone PEG-8 | | | | | | | 1 | 1.5 | 2 | 1 | 1.5 |
| Bis-PEG/PPG 18/6 Dimethicone | 1 | 1.5 | 2 | 1 | 1.5 | 2 | | | | | |
| Ethanol | | | | | | | | | | | |
| PEG-17 Dimethicone | | | | | | | | | | 1 | 1 |
| Glycerine | | | | 1 | 1 | 1 | | | | | |
| Isopropyl Alcohol | 70 | 70 | 70 | 70 | 70 | 70 | 70 | 70 | 70 | 70 | 70 |
| n-Propyl Alcohol | | | | | | | | | | | |
| Purified Water | 29 | 28.5 | 28 | 28 | 27.5 | 27 | 29 | 28.5 | 28 | 28 | 27.5 |

| INGREDIENTS | 106 | 107 | 108 | 109 | 110 | 111 | 112 | 113 | 114 | 115 |
|---|---|---|---|---|---|---|---|---|---|---|
| Dimethicone PEG-8 | 2 | | | | | | | 1 | 1.5 | 2 |
| Bis-PEG/PPG 18/6 Dimethicone | | 1 | 1.5 | 2 | 1 | 1.5 | 2 | | | |
| Ethanol | | 55 | 55 | 55 | 55 | 55 | 55 | 55 | 55 | 55 |
| PEG-17 Dimethicone | 1 | | | | | | | | | |
| Glycerine | | | | | 1 | 1 | 1 | | | |
| Isopropyl Alcohol | 70 | | | | | | | | | |
| n-Propyl Alcohol | | 10 | 10 | 10 | 10 | 10 | 10 | 10 | 10 | 10 |
| Purified Water | 27 | 34 | 33.5 | 33 | 33 | 32.5 | 32 | 34 | 33.5 | 33 |

Examples 116-136

| INGREDIENTS | 116 | 117 | 118 | 119 | 120 | 121 | 122 | 123 | 124 | 125 | 126 |
|---|---|---|---|---|---|---|---|---|---|---|---|
| Dimethicone PEG-8 | 1 | 1.5 | 2 | | | | | | | 1 | 1.5 |
| Bis-PEG/PPG 18/6 Dimethicone | | | | 1 | 1.5 | 1 | 1 | 1.5 | 2 | | |
| Ethanol | 55 | 55 | 55 | 65 | 65 | 65 | 65 | 65 | 65 | 65 | 65 |
| PEG-17 Dimethicone | | | | | | | | | | | |
| Glycerine | 1 | 1 | 1 | | | | 1 | 1 | 1 | | |
| n-Propyl Alcohol | 10 | 10 | 10 | | | | | | | | |
| Purified Water | 33 | 32.5 | 32 | 34 | 33.5 | 34 | 33 | 32.5 | 32 | 34 | 33.5 |

| INGREDIENTS | 127 | 128 | 129 | 130 | 131 | 132 | 133 | 134 | 135 | 136 |
|---|---|---|---|---|---|---|---|---|---|---|
| Dimethicone PEG-8 | 2 | | | | | | | 1 | 1.5 | 2 |
| Bis-PEG/PPG 18/6 Dimethicone | | 1 | 1.5 | 2 | 1 | 1.5 | 2 | | | |
| Ethanol | 65 | 65 | 65 | 65 | | | | | | |
| PEG-17 Dimethicone | | | | | | | | | | |
| Glycerine | | 1 | 1 | 1 | | | | 1 | 1 | 1 |
| n-Propyl Alcohol | | | | | 62 | 62 | 62 | 62 | 62 | 62 |
| Purified Water | 33 | 33 | 32.5 | 32 | 37 | 36.5 | 36 | 36 | 35.5 | 35 |

Examples 137-156

| INGREDIENTS | 137 | 138 | 139 | 140 | 141 | 142 | 143 | 144 | 145 | 146 |
|---|---|---|---|---|---|---|---|---|---|---|
| Cetrimonium Chloride | | | | | | | | | | |
| Dimethicone PEG-8 | 1 | 1.5 | 2 | 1 | 1.5 | 2 | | | | |
| Bis-PEG/PPG 18/6 Dimethicone | | | | | | | | | | 1.5 |
| Ethanol | | | | | | | 55 | 55 | 55 | |
| PEG-17 Dimethicone | | | | | | | | | | |
| Glycerine | | | | 1 | 1 | 1 | 1 | 1 | 1 | |
| n-Propyl Alcohol | 62 | 62 | 62 | 62 | 62 | 62 | 10 | 10 | 10 | 62 |
| Bis-PEG 12 Dimethicone | | | | | | | 3 | 4 | 5 | |
| Dihydroxypropyl PEG-5 Linoleammonium Chloride | | | | | | | | | | 0.1 |
| Purified Water | 37 | 36.5 | 36 | 36 | 35.5 | 35 | 31 | 30 | 29 | 36.4 |

| INGREDIENTS | 147 | 148 | 149 | 150 | 151 | 152 | 153 | 154 | 155 | 156 |
|---|---|---|---|---|---|---|---|---|---|---|
| Cetrimonium Chloride | 0.1 | | | | | 0.1 | | | | |
| Dimethicone PEG-8 | | | | | 0.5 | | | | | |
| Bis-PEG/PPG 18/6 Dimethicone | 5 | 5 | 1 | 2 | 1.5 | 3 | 3 | | | |
| Ethanol | | | 61 | 61 | 61 | 61 | 61 | 55 | 55 | 55 |
| PEG-17 Dimethicone | | | | | | | | | | |
| Glycerine | | | | | | | | | | |
| n-Propyl Alcohol | 62 | 62 | | | | | | 10 | 10 | 10 |
| Bis-PEG 12 Dimethicone | | | | | | | | 1 | 1.5 | 2 |
| Dihydroxypropyl PEG-5 Linoleammonium Chloride | | 0.1 | | | | | 0.1 | | | |
| Purified Water | 37.9 | 37.9 | 38 | 37 | 37 | 35.9 | 35.9 | 34 | 33.5 | 33 |

Examples 157-167

| INGREDIENTS | 157 | 158 | 159 | 160 | 161 | 162 | 163 | 164 | 165 | 166 | 167 |
|---|---|---|---|---|---|---|---|---|---|---|---|
| 1,3 Butylene Glycol Alcohol | | | | | | | | | | | |
| Behenamidopropyl Dimethylamine | | | | | | | | | | | |
| Behentrimonium Chloride | | | | | | | | | | | |
| Cetrimonium Chloride | 0.1 | | | | 0.1 | | | | | | 0.1 |
| Bis-PEG/PPG 18/6 Dimethicone | | | | | | | | | | | |
| Ethanol | 55 | 55 | 61 | 61 | 61 | 61 | 61 | | | | |
| Glycerine | | | | | | | | | | | |
| Cocoglucoside Glyceryl Oleate | | | | | | | | | | | |
| n-Propyl Alcohol | 10 | 10 | | | | | | 62 | 62 | 62 | 62 |
| Bis-PEG 12 Dimethicone | 1.5 | 1.5 | 1 | 1.5 | 2 | 1.5 | 1.5 | 1 | 1.5 | 2 | 1.5 |
| Dihydroxypropyl PEG-5 Linoleammonium Chloride | | 0.1 | | | | | 0.1 | | | | |
| Purified Water | 33.4 | 33.4 | 38 | 37.5 | 37 | 37.4 | 37.4 | 37 | 36.5 | 36 | 36.4 |

Examples 168-177

| INGREDIENTS | 168 | 169 | 170 | 171 | 172 | 173 | 174 | 175 | 176 | 177 |
|---|---|---|---|---|---|---|---|---|---|---|
| 1,3 Butylene Glycol | | 4.3 | 4.3 | 4.3 | 4.3 | 4.3 | 4.3 | 4.3 | | |
| Alcohol | | 62 | 62 | 62 | 62 | 62 | 62 | 62 | | |
| Behenamidopropyl Dimethylamine | | | | | | | | | 0.1 | |
| Behentrimonium Chloride | 0.1 | | | | | | | | | 0.1 |
| Cetrimonium Chloride | | | | | | | | | | |
| Bis-PEG/PPG 18/6 Dimethicone | | | | | | 1 | 1.5 | 2 | | |
| Ethanol | | | | | | | | | 61 | 61 |
| Glycerine | | 0.9 | 0.9 | 0.9 | 0.9 | 0.9 | 0.9 | 0.9 | | |
| Cocoglucoside Glyceryl Oleate | | 0.08 | 0.08 | 0.08 | 0.08 | 0.08 | 0.08 | 0.08 | | |
| n-Propyl Alcohol | 62 | 2 | 2 | 2 | 2 | 2 | 2 | 2 | | |
| Bis-PEG 12 Dimethicone | 1.5 | | 1 | 1.5 | 2 | | | | 2 | 2 |
| Dihydroxypropyl PEG-5 Linoleammonium Chloride | | | | | | | | | | |
| Purified Water | 36.4 | 30.7 | 29.7 | 29.2 | 28.7 | 29.7 | 29.2 | 28.7 | 36.9 | 36.9 |

Examples 178-188

| INGREDIENTS | 178 | 179 | 180 | 181 | 182 | 183 | 184 | 185 | 186 | 187 | 188 |
|---|---|---|---|---|---|---|---|---|---|---|---|
| 1,3-butylene glycol | | | 4.3 | 4.3 | 4.3 | 4.3 | | 0.43 | 0.43 | 0.43 | 0.43 |
| Ethanol | | | 62 | 62 | 62 | 62 | | 70 | 70 | 70 | 70 |
| Behenoyl PG-Trimonium Chloride | | 0.1 | | | | | | | | | |
| Cetearyl Alcohol &Behentrimonium Chloride | 0.1 | | | | | | | | | | |
| Behentrimonium Chloride | | | | | | | | | | | |
| Cetrimonium Chloride | | | | | | | | 0.1 | 0.1 | 0.1 | |
| Dimethicone PEG-8 | | | | 0.5 | 0.5 | | | 0.5 | | 0.5 | |
| Bis-PEG/PPG 15/15 Dimethicone | | | | | | | | | | | |
| Bis-PEG/PPG 18/6 Dimethicone | | | 0.5 | 0.75 | | 2 | | | | | |
| Ethanol | 61 | 61 | | | | | | | | | |
| PEG-17 Dimethicone | | | | | | | | | | | |
| Glycerine | | | 0.9 | 0.9 | 0.9 | 0.9 | | 0.9 | 0.9 | 0.9 | 0.9 |
| Isopropyl Alcohol | | | | | | | | | | | |
| Cocoglucoside & Glyceryl Oleate | | | 0.08 | 0.08 | 0.08 | 0.08 | | 0.08 | 0.08 | 0.08 | 0.08 |
| n-Propyl Alcohol | | | 2 | 2 | 2 | 2 | | 2 | 2 | | |
| PEG-200 Hydrogenated Glyceryl Palmate | | | | | | | | | | | |
| Bis-PEG 12 Dimethicone | 2 | 2 | 0.5 | 0.75 | 2 | | | 2.5 | 2.5 | 2.5 | 2.5 |
| Purified Water | 36.9 | 36.9 | 29.7 | 29.2 | 28.2 | 28.2 | 100 | 23.5 | 24 | 25.5 | 26.1 |

Examples 189-198

| INGREDIENTS | 189 | 190 | 191 | 192 | 193 | 194 | 195 | 196 | 197 | 198 |
|---|---|---|---|---|---|---|---|---|---|---|
| 1,3-butylene glycol | | 0.43 | 0.43 | 0.43 | 0.43 | 0.43 | 0.43 | | | |
| Ethanol | 55 | 62 | 62 | 70 | 70 | 70 | 70 | | | |
| Behenoyl PG-Trimonium Chloride | | | | | | | | | | |
| Cetearyl Alcohol &Behentrimonium Chloride | | | | | | | | | | |
| Behentrimonium Chloride | 0.1 | 0.1 | 0.1 | | | | | | | |
| Cetrimonium Chloride | 0.1 | 0.1 | 0.1 | 0.1 | 0.1 | 0.1 | 0.1 | | | |
| Dimethicone PEG-8 | 2 | | | | | | | | | |
| Bis-PEG/PPG 15/15 Dimethicone | | | | | 2.5 | 2.5 | | | 2 | 2 |
| Bis-PEG/PPG 18/6 Dimethicone | | | | | | | | | | |

-continued

| INGREDIENTS | 189 | 190 | 191 | 192 | 193 | 194 | 195 | 196 | 197 | 198 |
|---|---|---|---|---|---|---|---|---|---|---|
| Ethanol | | | | | | | | 61 | 55 | 61 |
| PEG-17 Dimethicone | | | | | | | | 2 | | |
| Glycerine | | 0.9 | 0.9 | 0.9 | 0.9 | 0.9 | 0.9 | | | |
| Isopropyl Alcohol | | | | | | | | | | |
| Cocoglucoside & Glyceryl Oleate | | 0.08 | 0.08 | 0.08 | 0.08 | 0.08 | 0.08 | | | |
| n-Propyl Alcohol | 10 | 2 | 2 | | | | | | 10 | |
| PEG-200 Hydrogenated Glyceryl Palmate | | | | 0.1 | 0.5 | 0.5 | 0.5 | | | |
| Bis-PEG 12 Dimethicone | | 2.5 | 2 | 2.5 | 2.5 | | | | | |
| Purified Water | 32.8 | 31.9 | 32.4 | 25.9 | 25.5 | 25.5 | 25.5 | 37 | 33 | 37 |

Examples 199-219

| INGREDIENTS | 199 | 200 | 201 | 202 | 203 | 204 | 205 | 206 | 207 | 208 | 209 |
|---|---|---|---|---|---|---|---|---|---|---|---|
| 1,3 Butylene Glycol | | | 0.43 | | 0.43 | | | | | | |
| Cetearyl Alcohol and Behentrimonium Chloride | | | | 1 | | | | | | | |
| Behentrimonium Chloride | | | 0.1 | | 0.1 | | | | | | |
| Bis-PEG/PPG 18/6 Dimethicone | | | | 1 | | | | | | | |
| Ethanol | 55 | 55 | 70 | 55 | 70 | 55 | 55 | 55 | 55 | 55 | 55 |
| PEG-17 Dimethicone | 2 | 1 | | 1 | | 2 | | | 1 | | 1 |
| Glycerine | | | 0.9 | | 0.9 | | | | | | |
| Cocoglucoside Glyceryl Oleate | | | 0.08 | | 0.08 | | | | | | |
| n-Propyl Alcohol | 10 | 10 | | 10 | | 10 | 10 | 10 | 10 | 10 | 10 |
| PEG-200 Hydrogenated Glyceryl Palmate | | | 1 | | | | | | | | |
| Bis-PEG 20 Dimethicone | | | | | | | 2 | | | 1 | 1 |
| Bis-PEG 12 Dimethicone | | 1 | 2.5 | | 2.5 | | | 2 | 1 | 1 | |
| Purified Water | 43 | 43 | 25 | 43 | 25 | 43 | 43 | 43 | 43 | 43 | 43 |

| INGREDIENTS | 210 | 211 | 212 | 213 | 214 | 215 | 216 | 217 | 218 | 219 |
|---|---|---|---|---|---|---|---|---|---|---|
| 1,3 Butylene Glycol | | | | | | | | | | |
| Cetearyl Alcohol and Behentrimonium Chloride | | | | | | | | | | |
| Behentrimonium Chloride | | | | | | | | | | |
| Bis-PEG/PPG 18/6 Dimethicone | | | | | | | | | | |
| Ethanol | 62 | 62 | 62 | 62 | 62 | 62 | 70 | 70 | 70 | 70 |
| PEG-17 Dimethicone | 2 | | | 1 | | 1 | 2 | | | 1 |
| Glycerine | | | | | | | | | | |
| Cocoglucoside Glyceryl Oleate | | | | | | | | | | |
| n-Propyl Alcohol | 2 | 2 | 2 | 2 | 2 | 2 | | | | |
| PEG-200 Hydrogenated Glyceryl Palmate | | | | | | | | | | |
| Bis-PEG 20 Dimethicone | | 2 | | | 1 | 1 | | 2 | | |

-continued

| | | | | | | | | | | |
|---|---|---|---|---|---|---|---|---|---|---|
| Bis-PEG 12 Dimethicone | | 2 | 1 | 1 | | | | 2 | 1 | |
| Purified Water | 36 | 36 | 36 | 36 | 36 | 36 | 28 | 28 | 28 | 28 |

Examples 220-230

| INGREDIENTS | 220 | 221 | 222 | 223 | 224 | 225 | 226 | 227 | 228 | 229 | 230 |
|---|---|---|---|---|---|---|---|---|---|---|---|
| PEG-8 Dimethicone | | | 0.01 | 0.01 | 0.05 | 0.01 | 0.01 | 0.05 | 0.01 | 0.01 | 0.01 |
| Ethanol | 70 | 70 | 62 | 62 | 62 | 70 | 70 | 70 | 60 | 60 | 60 |
| PEG-17 Dimethicone | | 1 | | | | | | | | | |
| n-Propyl Alcohol | | | 2 | 2 | 2 | 2 | 2 | 2 | 10 | 10 | 10 |
| Bis-PEG 20 Dimethicone | 1 | 1 | | | | | | | | | |
| Bis-PEG-12 Dimethicone | 1 | | 1 | 1 | 1 | 1 | 1 | 1 | 1 | 1 | 1 |
| Purified Water | 28 | 28 | 35 | 35 | 35 | 27 | 27 | 27 | 29 | 29 | 29 |

Examples 231-240

| INGREDIENTS | 231 | 232 | 233 | 234 | 235 | 236 | 237 | 238 | 239 | 240 |
|---|---|---|---|---|---|---|---|---|---|---|
| PEG-8 Dimethicone | 0.01 | 0.01 | 0.05 | 0.01 | 0.01 | 0.05 | 0.01 | 0.01 | 0.05 | 0.01 |
| Ethanol | | | | 55 | 55 | 55 | 65 | 65 | 65 | 61 |
| PEG-17 Dimethicone | | | | | | | | | | |
| n-Propyl Alcohol | 60 | 60 | 60 | 10 | 10 | 10 | 10 | 10 | 10 | 39 |
| Bis-PEG 20 Dimethicone | | | | | | | | | | |
| Bis-PEG-12 Dimethicone | 1 | 1 | 1 | 1 | 1 | 1 | 1 | 1 | 1 | 1 |
| Purified Water | 39 | 39 | 39 | 34 | 34 | 34 | 24 | 24 | 24 | −1 |

Examples 241-251

| INGREDIENTS | 241 | 242 | 243 | 244 | 245 | 246 | 247 | 248 | 249 | 250 | 251 |
|---|---|---|---|---|---|---|---|---|---|---|---|
| PEG-8-Dimethicone | 0.01 | 0.05 | | | | | | | | | |
| Bis-PEG/PPG 18/6 Dimethicone | | | | | | | | | 1 | 1 | 1 |
| Ethanol | 61 | 61 | 55 | 65 | 61 | | 70 | 62 | 60 | 65 | 65 |
| DEA C8-C18 Perfluoroalkylethyl Phosphate | | | | | | | | | | | |
| Ammonium C6-C16 Perfluoroalkylethyl Phosphate | | | | | | | | | 1 | 1 | 1 |
| Cetrimonium Chloride | | | | | | | | | | | |
| Dihydroxypropyl PEG-5 Linoleammonium Chloride | | | | | | | | | | | |
| n-Propyl Alcohol | | | 10 | 10 | | 60 | 2 | 2 | 10 | 10 | 10 |
| Bis PEG 12-Dimethicone | 1 | 1 | 1 | 1 | 1 | 1 | 1 | 1 | 1 | | |
| Purified Water | 38 | 38 | 34 | 24 | 38 | 39 | 27 | 35 | 27 | 22 | 23 |

Examples 252-261

| INGREDIENTS | 252 | 253 | 254 | 255 | 256 | 257 | 258 | 259 | 260 | 261 |
|---|---|---|---|---|---|---|---|---|---|---|
| PEG-8-Dimethicone | | | | | | | | | | |
| Bis-PEG/PPG 18/6 Dimethicone | 1 | 1 | | 1.5 | | | | | | |
| Ethanol | 65 | 65 | 65 | 65 | 61 | 61 | 61 | 61 | 61 | 61 |
| DEA C8-C18 Perfluoroalkylethyl Phosphate | 1 | 1 | | | | | | | | |
| Ammonium C6-C16 Perfluoroalkylethyl Phosphate | | | | | | | | | | |
| Cetrimonium Chloride | | | | | 0.1 | 0.5 | 1 | 0.1 | 0.5 | 1 |
| Dihydroxypropyl PEG-5 Linoleammonium Chloride | | | | | | | | 0.1 | 0.5 | 1 |
| n-Propyl Alcohol | 10 | 10 | 10 | 10 | | | | | | |
| Bis PEG 12-Dimethicone | | 1 | 1.5 | | 1 | 1 | 1 | | | |
| Purified Water | 23 | 22 | 23.5 | 23.5 | 37.9 | 37.5 | 37 | 38.8 | 38 | 37 |

Examples 262-272

| INGREDIENTS | 262 | 263 | 264 | 265 | 266 | 267 | 268 | 269 | 270 | 271 | 272 |
|---|---|---|---|---|---|---|---|---|---|---|---|
| Behenyl PG-Trimonium Chloride | | | | | | | | | | | |
| Cetearyl Alcohol and Behentrimonium Chloride | | | | | | | | | | | |
| Polyethylene Glycol 600 | | | | 0.1 | 0.5 | 1 | | | | | |
| PEG-7 Glyceryl Cocoate | | | | | | | | | | | |
| Ethanol | 61 | 61 | 61 | 61 | 61 | 61 | 61 | 61 | 61 | 61 | 61 |
| Cocoglucoside & Glyceryl Oleate | | | | | | | | | | 0.1 | 0.5 |
| Polyethylene Glycol | 0.2 | 0.5 | 1 | | | | | | | | |
| PEG-200 Hydrogenated Glyceryl Palmate | | | | | | | 0.1 | 0.5 | 1 | | |
| Bis-PEG 12 Dimethicone | 1 | 1 | 1 | 1 | 1 | 1 | 1 | 1 | 1 | 1 | 1 |
| Purified Water | 37.8 | 37.5 | 37 | 37.9 | 37.5 | 37 | 37.9 | 37.5 | 37 | 37.9 | 37.5 |

Examples 273-282

| INGREDIENTS | 273 | 274 | 275 | 276 | 277 | 278 | 279 | 280 | 281 | 282 |
|---|---|---|---|---|---|---|---|---|---|---|
| Behenyl PG-Trimonium Chloride | | | | 0.1 | 0.5 | 1 | | | | |
| Cetearyl Alcohol and Behentrimonium Chloride | | | | | | | 0.1 | 0.5 | 1 | |
| Polyethylene Glycol 600 | | | | | | | | | | |
| PEG-7 Glyceryl Cocoate | | | | | | | | | | 0.1 |
| Ethanol | 61 | 61 | 61 | 61 | 61 | 61 | 61 | 61 | 61 | 61 |
| Cocoglucoside & Glyceryl Oleate | 1 | | | | | | | | | |
| Polyethylene Glycol | | | | | | | | | | |
| PEG-200 Hydrogenated Glyceryl Palmate | | | | | | | | | | |
| Bis-PEG 12 Dimethicone | 1 | 2 | 3 | 1 | 1 | 1 | 1 | 1 | 1 | 1 |
| Purified Water | 37 | 37 | 36 | 37.9 | 37.5 | 37 | 37.9 | 37.5 | 37 | 37.9 |

Examples 283-293

| INGREDIENTS | 283 | 284 | 285 | 286 | 287 | 288 | 289 | 290 | 291 | 292 | 293 |
|---|---|---|---|---|---|---|---|---|---|---|---|
| Behenyl PG-Trimonium Chloride | | | 0.2 | 0.25 | 0.2 | 0.25 | | | | 0.2 | 0.2 |

-continued

| INGREDIENTS | 283 | 284 | 285 | 286 | 287 | 288 | 289 | 290 | 291 | 292 | 293 |
|---|---|---|---|---|---|---|---|---|---|---|---|
| Cetearyl Alcohol and Behentrimonium Chloride | | | 0.3 | 0.4 | 0.3 | 0.4 | | | | 0.3 | 0.3 |
| PEG-7 Glyceryl Cocoate | 0.5 | 1 | 0.15 | 0.2 | 0.15 | 0.2 | | | | 0.15 | 0.15 |
| PEG-PPG 20/6 Dimethicone | | | | | | | | | 1 | | |
| PEG 4-Dimethicone | | | | | | | 1 | | | | |
| PEG-8-Dimethicone | | | | | | | | 1 | | | |
| Ethanol | 61 | 61 | 61 | 61 | 65 | 65 | 65 | 65 | 65 | 61 | 61 |
| Cocoglucoside & Glyceryl Oleate | | | 0.2 | 0.25 | 0.2 | 0.25 | | | | 0.2 | 0.2 |
| Cetrimonium Chloride | | | 0.1 | 0.2 | 0.1 | 0.2 | | | | 0.1 | 0.1 |
| Dihydroxypropyl PEG-5 Linoleammonium Chloride | | | 0.4 | 0.5 | 0.4 | 0.5 | | | | 0.4 | 0.4 |
| n-Propyl Alcohol | | | | | 10 | 10 | 10 | 10 | 10 | | |
| PEG-200 Hydrogenated Glyceryl Palmate | | | 0.15 | 0.2 | 0.15 | 0.2 | | | | 0.15 | 0.15 |
| Bis-PEG 12 Dimethicone | 1 | 1 | 2 | 2 | 2 | 3 | | | | 1.5 | 1 |
| Purified Water | 37.5 | 37 | 35.5 | 35 | 21.5 | 20 | 24 | 24 | 24 | 36 | 36.5 |

What is claimed is:

1. A foamable alcohol composition, comprising:
   a) a $C_{1-4}$ alcohol, or mixtures thereof, present in an amount greater than or equal to 60% v/v of the total composition;
   b) an effective physiologically acceptable silicone-based surface active agent for foaming and wetting selected from the group consisting of bis-PEG-[6-9] dimethicones, organofunctional siloxanes, linear and/or multifunctional silicone polyethers, silicone sulfosuccinates, silicone alcohol alkoxylates, silicone taurine derivatives, silicone phosphobetaines, silicone quats and combinations thereof, present in an amount of at least 0.01% by weight of the total composition; and
   c) water present in an amount to balance the total composition to 100% by weight of the total composition;
wherein said alcohol composition optionally includes no more than 1% by weight of at least one additional surfactant for adjusting properties of the foam produced from the composition;
wherein the alcohol composition is mixed with air at low pressure to form a foam.

2. The foamable alcohol composition according to claim 1 wherein said composition further includes said at least one additional surfactant for adjusting properties of foam produced from the composition.

3. The foamable alcohol composition according to claim 2 wherein the additional surfactant is selected from the group consisting of additional silicone-based surface active agents, fluorinated surfactants, alkylglucosides, poly(ethoxylated and/or propoxylated)alcohol, a poly(ethoxylated and/or propoxylated)ester, polyethoxylated fatty alcohol, an alkenyl alcohol, an ester of a polyhydric alcohol, an ether of a polyhydric alcohol, an ester of a polyalkoxylated polyhydric alcohol, an ether of a polyalkoxylated polyhydric alcohol, a sorbitan fatty acid ester, a polyalkoxylated sorbitan fatty acid ester, a betaine, a sulfobetaine, an imidazoline, an amino acid, a lecithin, a phosphatide, an amine oxide, a sulfoxide and mixtures thereof.

4. The foamable alcohol composition according to claim 3 wherein the betaine is cocamidopropyl betaine.

5. The foamable alcohol composition according to claim 3 wherein the alkylglucoside is cocoglucoside.

6. The foamable alcohol composition according to claim 3 wherein the polyethoxylated fatty alcohol is polyethoxylated stearyl alcohol (21 moles ethylene oxide).

7. The foamable alcohol composition according to claim 3 wherein the polyethoxylated fatty alcohol is polyethoxylated stearyl alcohol (2 moles ethylene oxide).

8. The foamable alcohol composition according to claim 3 wherein the polyethoxylated fatty alcohol is a combination of polyethoxylated stearyl alcohol (21 moles ethylene oxide) and polyethoxylated stearyl alcohol (2 moles ethylene oxide).

9. The foamable alcohol composition according to claim 3 wherein said fluorinated surfactant is DEA C[8-18] perfluoroalkylethyl phosphate.

10. The foamable alcohol composition according to claim 3 wherein said fluorinated surfactant is ammonium C[6-16] perfluoroalkylethyl phosphate.

11. The foamable alcohol composition according to claim 1, further comprising a foam stabilizing agent selected from the group consisting of
    lactic acid esters of monoglycerides,
    cationic emulsifiers,
    quaternary ammonium compounds,
    triquaternized stearic phospholipid complex,
    hydroxystearamide propyltriamine salts,
    lactic acid monoglycerides,
    food emulsifiers selected from the group consisting of glyceryl monostearate, propylene glycol monostearate, and sodium stearoyllactylate,
    cetyl betaine,
    glycolether
    glycerine,
    butyleneglycol,
    silicone wax, an encapsulated oil,
microcapsule mineral oil,
and combinations thereof.

12. The foamable alcohol composition according to claim 11 wherein the foam stabilizing agent is selected from the group consisting of glycolether, glycerine, butyleneglycol, behentrimonium chloride, cetrimonium chloride and combinations thereof.

13. A method of forming a foam using a foamable alcohol composition according to claim 1, by storing said composition in a container having a dispenser pump, activating the dispenser pump to mix the alcohol and silicone-based surface active agent mixture with air under low pressure conditions to form an alcohol foam which is dispensed from said container.

14. A foamable alcohol composition, comprising:
  a) ethanol present in a range from about 60 to about 85% v/v;
  b) an effective physiologically acceptable silicone-based surface active agent selected from the group consisting of Bis-PEG-[6-20] dimethicone, 3-(3-hydroxypropyl) heptamethyltrisiloxane ethoxylated acetate; a bis-PEG/PPG 18/6 dimethicone; polyether-modified polysiloxanes; polysiloxane betaines; organofunctional siloxanes and combinations thereof, present in a range from about 0.01% to about 10.0% by weight of the total composition; and
  c) a foam stabilizing agent; and
  d) water present in an amount to balance the total composition to 100% by weight;
wherein said alcohol composition optionally includes no more than 1% by weight of at least one additional surfactant for adjusting properties of the foam produced from the composition;
wherein the alcohol composition is mixed with air at low pressure to form a foam.

15. The foamable alcohol composition according to claim 14 wherein said foam stabilizing agent is behentrimonium chloride present in a the composition range from about 0.05 to about 1.0% by weight of the total composition, and further including n-propyl alcohol present in an amount from about 1 to about 60% v/v of the total composition, wherein a sum total of n-propyl alcohol and ethanol is at least 60% and at most 85% of the total composition; dihydroxypropyl PEG-5 linoleammonium chloride present in a range from about 0.05 to about 1.5% by weight, PEG-200 hydrogenated glyceryl palmate and PEG-7 glyceryl cocoate present in a range from about 0.05 to about 1.5% of the total composition, and cocoglucoside and glyceryl oleate present in a range from about 0.05 to about 1.5% by weight of the total composition.

* * * * *